(12) United States Patent
Ruckh et al.

(10) Patent No.: US 10,197,498 B2
(45) Date of Patent: Feb. 5, 2019

(54) COMPOSITIONS AND METHODS FOR MEASUREMENT OF ANALYTES

(71) Applicant: Northeastern University, Boston, MA (US)

(72) Inventors: Timothy T. Ruckh, Somerville, MA (US); Mary K. Balaconis, South Boston, MA (US); Heather A. Clark, Lexington, MA (US); Christopher Skipwith, Quincy, MA (US)

(73) Assignee: Northeastern University, Boston, MA (US)

( * ) Notice: Subject to any disclaimer, the term of this patent is extended or adjusted under 35 U.S.C. 154(b) by 372 days.

(21) Appl. No.: 15/030,698

(22) PCT Filed: Oct. 21, 2014

(86) PCT No.: PCT/US2014/061652
§ 371 (c)(1),
(2) Date: Apr. 20, 2016

(87) PCT Pub. No.: WO2015/061371
PCT Pub. Date: Apr. 30, 2015

(65) Prior Publication Data
US 2016/0274030 A1    Sep. 22, 2016

Related U.S. Application Data

(60) Provisional application No. 61/893,587, filed on Oct. 21, 2013.

(51) Int. Cl.
A61B 5/00 (2006.01)
G01N 21/64 (2006.01)
(Continued)

(52) U.S. Cl.
CPC ........ G01N 21/6428 (2013.01); C12M 23/20 (2013.01); C12M 23/54 (2013.01);
(Continued)

(58) Field of Classification Search
CPC ... A61B 5/0059; A61B 5/0071; A61B 5/0095; A61B 5/1455; A61B 5/14503;
(Continued)

(56) References Cited

U.S. PATENT DOCUMENTS

| 7,485,591 B2 | 2/2009 | Frey et al. |
| 2007/0114138 A1* | 5/2007 | Krasteva ............ G01N 27/126 205/787 |

(Continued)

FOREIGN PATENT DOCUMENTS

WO    WO-2013134401 A2    9/2013

OTHER PUBLICATIONS

Adrogue, H.J. and Madias, N.E., "Hypernatremia," N Engl J Med, vol. 342, pp. 1493-1499 (2000).
(Continued)

*Primary Examiner* — Eric Winakur
*Assistant Examiner* — Chu Chuan (JJ) Liu
(74) *Attorney, Agent, or Firm* — Dana M. Gordon; Foley Hoag LLP

(57) ABSTRACT

Disclosed herein sensor matrices comprising nanofibers and one or more sensor components, wherein the one or more sensor components detect an analyte. In addition, methods of making and detecting the sensor matrices are disclosed. For example, a nanofiber with a shell and coaxial core may be made with a sensor in the shell.

20 Claims, 23 Drawing Sheets

(51) Int. Cl.

| | |
|---|---|
| *C12M 1/00* | (2006.01) |
| *C12M 1/12* | (2006.01) |
| *C12M 1/34* | (2006.01) |
| *G01N 33/543* | (2006.01) |
| *C12M 3/00* | (2006.01) |
| *G01N 33/53* | (2006.01) |

(52) U.S. Cl.
CPC ............ *C12M 25/14* (2013.01); *C12M 41/36* (2013.01); *C12M 41/46* (2013.01); *G01N 33/5308* (2013.01); *G01N 33/54346* (2013.01); *G01N 2021/6441* (2013.01)

(58) Field of Classification Search
CPC ............ A61B 5/14865; A61B 5/14556; A61B 5/6848; G01N 21/6428
See application file for complete search history.

(56) References Cited

U.S. PATENT DOCUMENTS

| | | | |
|---|---|---|---|
| 2008/0193956 A1* | 8/2008 | Kricka ............... | G01N 21/6428 435/8 |
| 2010/0197039 A1* | 8/2010 | Zang .................. | G01N 21/6428 436/172 |
| 2010/0285972 A1 | 11/2010 | Dubrow et al. | |
| 2012/0222958 A1 | 9/2012 | Pourmand et al. | |
| 2013/0122531 A1* | 5/2013 | Chaniotakis ......... | G01N 33/551 435/14 |
| 2013/0197326 A1 | 8/2013 | Dubach et al. | |
| 2016/0041135 A1* | 2/2016 | Lannutti ............ | G01N 21/6408 435/29 |

OTHER PUBLICATIONS

Adrogue, H.J. and Madias, N.E., "Hypernatremia," N Engl J Med, vol. 342, pp. 1581-1589 (2000).
Bakker, et al., "Carrier-Based Ion-Selective Electrodes and Bulk Optodes. 1. General Characteristics," Chem. Rev., vol. 97, pp. 3083-3132 (1997).
Benvenga, S., "What is the Pathogenesis of Hyponatremia After Subarachnoid Hemorrhage?" Nat. Clin. Pract. Endocrinol. Metab., vol. 2, pp. 608-609 (2006).
Billingsley, et al., "Fluorescent Nano-Optodes for Glucose Detection," Anal. Chem., vol. 82, No. 9, pp. 3707-3713 (2010).
Crank, J, *The Mathematics of Diffusion* (Oxford Univ Press, New York), Chs. 5, 6 and 7, 75 pages (1975).
Ellison, D.H. and Berl, T., "The Syndrome of Inappropriate Antidiuresis," N Engl J Med, vol. 356, pp. 2064-2072 (2007).
Hynd, et al. "Functionalized Hydrogel Surfaces for the Patterning of Multiple Biomolecules," J Biomed Mater Res, vol. 81, pp. 347-354 (2007).
International Search Report and Written Opinion issued by the U.S. Patent and Trademark Office for International Patent Application No. PCT/US14/61652 dated Jan. 14, 2015 (15 pgs.).
Neises, B. and Steglich, W., "Simple Method for the Esterification of Carboxylic Acids," Angew Chem Int.Ed Engl, vol. 17, No. 7, pp. 522-524 (Jul. 1978).

* cited by examiner

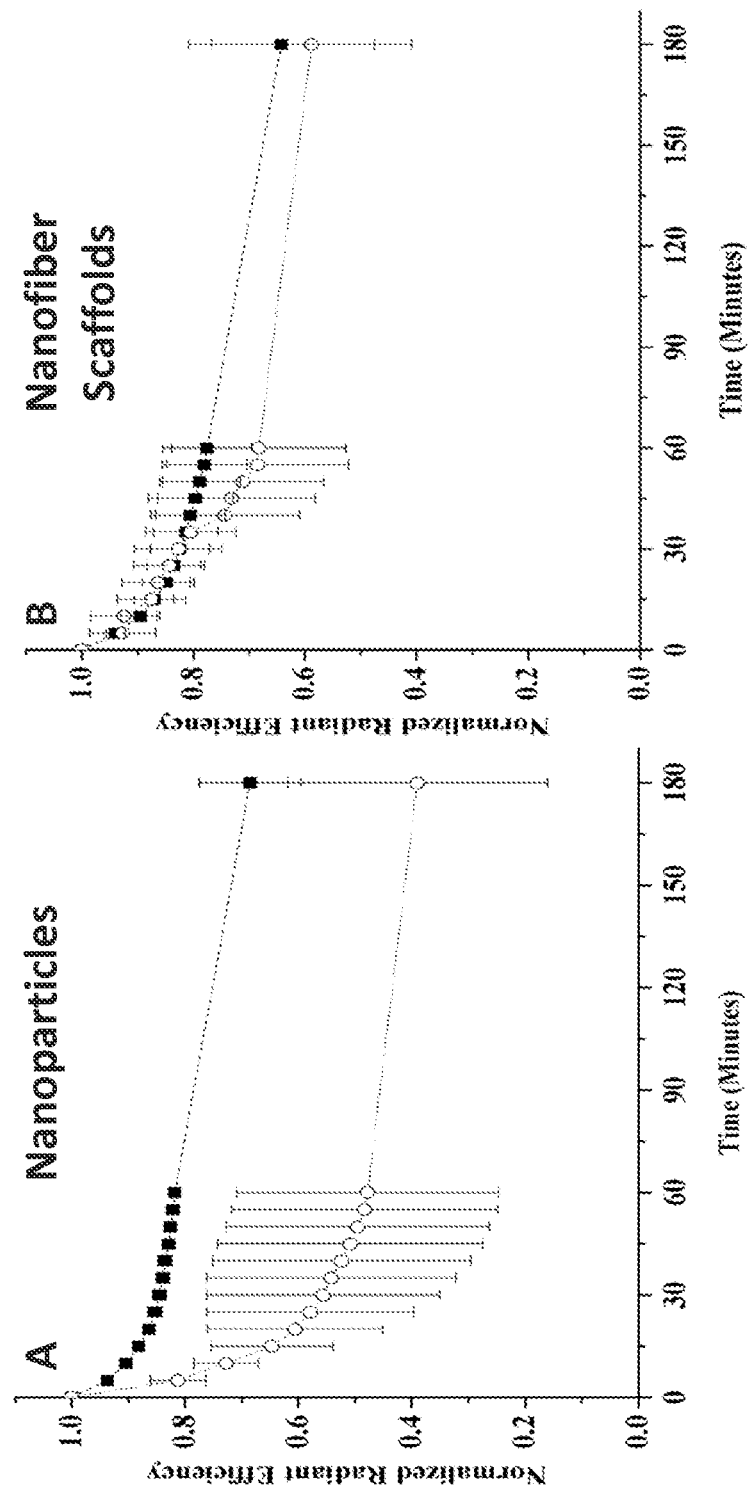

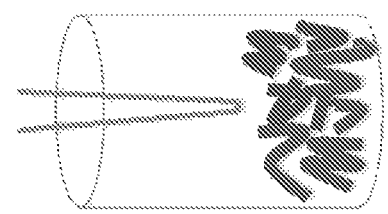
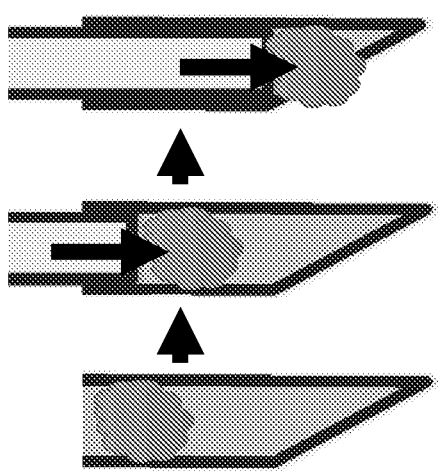
Fig. 9B
Fig. 9A

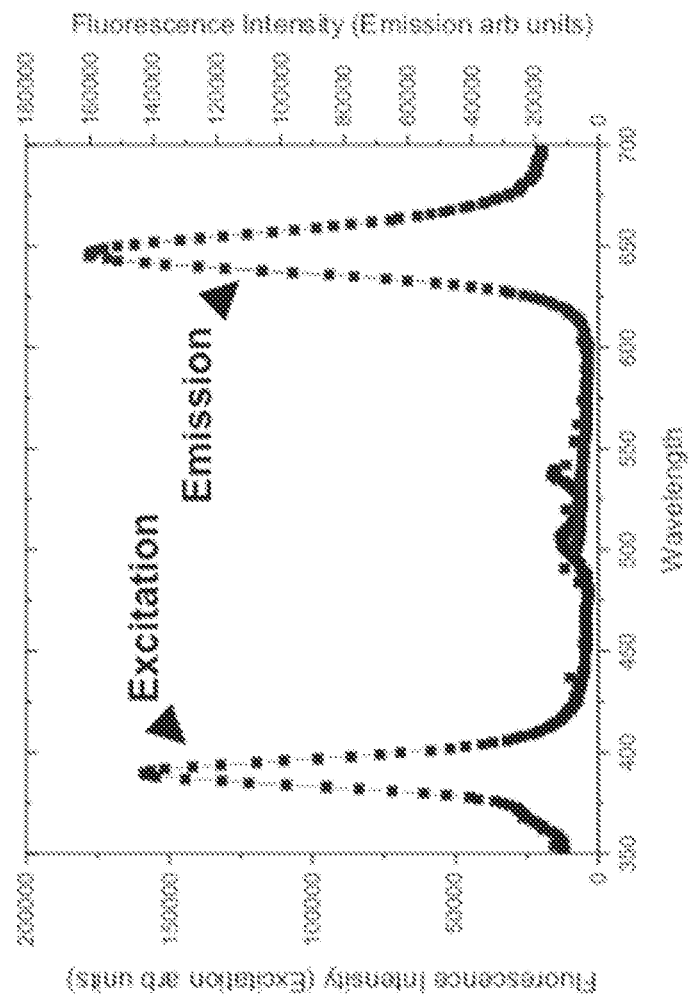
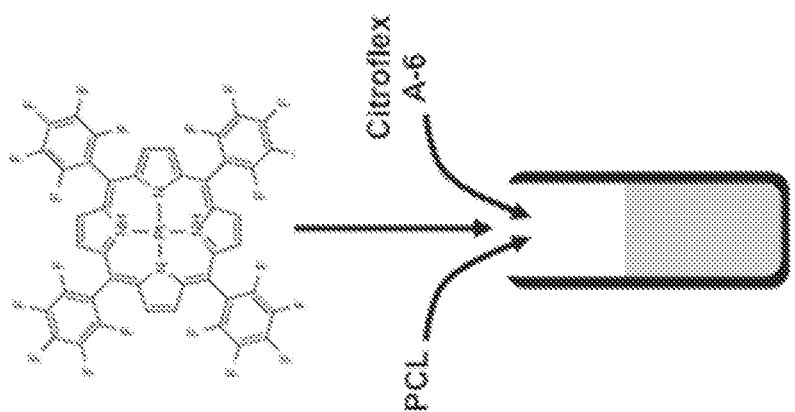
Fig. 14

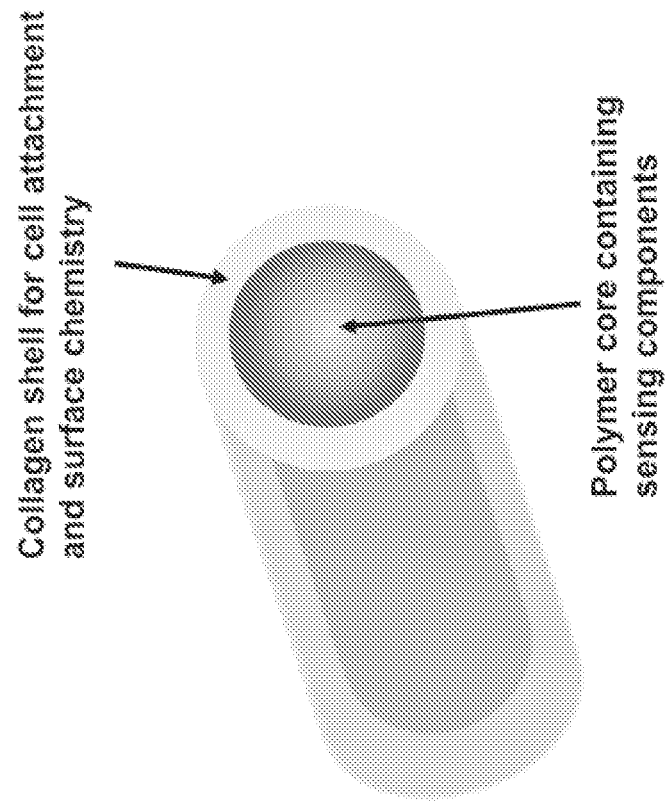
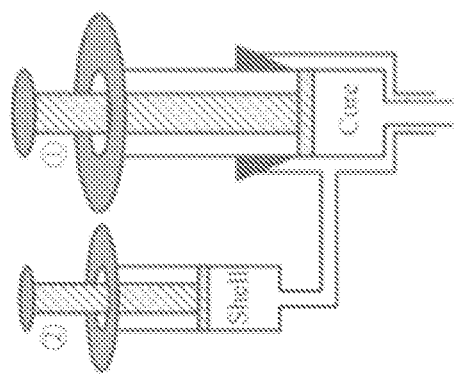
Fig. 15

COMPOSITIONS AND METHODS FOR MEASUREMENT OF ANALYTES

CROSS-REFERENCE TO RELATED APPLICATION

This application is a National Stage Entry of PCT International Application No. PCT/US14/61652, filed Oct. 21, 2014, which claims the benefit of U.S. Provisional Application No. 61/893,587, filed Oct. 21, 2013, the contents of which are incorporated herein by reference.

FIELD OF THE INVENTION

The present application is generally directed to compositions and methods for measuring analytes in vivo and in vitro using fibrous materials.

BACKGROUND OF THE INVENTION

Analyte detection is an important component in biotechnology, analytical chemistry, analysis of environmental samples, and medical diagnostics. Certain types of detection assays, such as fluorescence-based assays, are capable of providing detailed pictures of where fluorescent molecules are localized in tissues and cells. In particular, fluorescence-based assays exhibit exceptional sensitivity, detecting small concentrations of fluorescent molecules.

In addition, direct, minimally invasive monitoring of in vivo physiological conditions presents a route to determine health status in real time and address needs as they arise. Continuously monitoring sodium in vivo addresses multiple diseases and could prevent clinical complications during certain procedures. Sodium imbalances may lead to hypernatremia (Adrogue H J, Madias N E (2000) *N Engl J Med* 342:1483-1499) or hyponatremia (Adrogue H J, Madias N E (2000) *N Engl J Med* 342:1581-1589)—the most common electrolyte disorder. Monitoring sodium may provide an insight into the progression of subarachnoid hemorrhage or syndrome of inappropriate antidiuresis (Benvenga S (2006) *Nat Clin Pract Endocrinol Metab* 2:608-609; Ellison D H, Berl T (2007) *N Engl J Med* 356:2064-2072). However, to provide continuous monitoring, sensors need to be small enough to have a rapid response to changes in concentration yet be large enough to reside at the sight of administration without diffusing away or being endocytosed/phagocytosed by cells.

However, the only commercially available methods to measure analytes are through blood withdrawals and detection through either a glucometer or ELISA detection kit. These approaches require the removal of blood and can only be made when blood is drawn. Furthermore, presently available approaches utilize sensors that are insufficient for in vivo monitoring of analytes because the sensors do not remain at the site of administration and therefore do not provide an opportunity to detect the sensors.

Previous in vivo studies with fluorescent nanosensors were limited because of sensor diffusion away from and cellular uptake at the injection site. Alternative approaches that include altering sensing geometry into microworms and gel encapsulation of sensors prolonged in vivo sensing, but could not be sufficiently mass produced or had a limited lifetime, respectively.

Therefore, there is a need for devices, compositions and methods for the inexpensive and rapid assaying of biological, environmental, and chemical samples. Moreover, there is a need for sensing devices that can be mass produced and devices that limit cellular uptake and diffusion of the sensors in vivo.

SUMMARY OF THE INVENTION

The present application describes the fabrication and application of fibrous sensors either as a scaffold or individual fibers that allow localized monitoring of analytes both in vitro and in vivo. Electrospun fibrous sensors as described herein can be used to enlarge the sensing implant and potentially limit cellular uptake and diffusion of the sensors in vivo.

According to aspects of the present disclosure, sensor matrices are described having a shape that allows for sustained localization of optode sensing agents at a site of in vivo administration of the sensing agents in a tissue. The sensor matrices may have a particular shape or structure that provides a high surface-to-volume ratio that allows for accurate measurement of analytes and for reduced dispersion of sensing agents in the tissue of administration. Aspects of the invention also involve methods of measuring the fluorescence in a sample utilizing the sensing agents disclosed herein. Furthermore, the compositions and methods disclosed herein provide for rapid and simple measurement of analytes in tissues, such as epithelial and endothelial tissues.

Aspects disclosed herein provide a fibrous sensor matrix. The sensor matrix includes nanofibers and one or more sensor components, wherein the one or more sensor components detect an analyte, and in certain embodiments, the matrix has a surface area to volume ratio of at least 100 $mm^{-1}$ with a width of about 200 nm to about 500 nm and a length being greater than the width. In certain embodiments, the one or more sensors covalently bind to the analyte. In particular embodiments, the analyte is selected from the group consisting of electrolytes, proteases, hormones, steroids, small molecules, drugs, and saccharides. In other embodiments, the one or more sensors are fluorescent sensors or sensors for photoacoustic imaging.

In some embodiments, the nanofibers comprise a polymer. In certain embodiments, the nanofibers also include a plasticizer. In other embodiments, the nanofiber comprises a core and shell. In more embodiments, the nanofiber comprises a biocompatible shell. In further embodiments, the shell is permeable to analyte and impermeable to the one or more sensors.

In still further embodiments, the nanofiber comprises one or more polymers selected from the group consisting of polyvinyl chloride, polylactic co-glycolic acid, methacrylate, and polycaprolactone.

In particular embodiments, the sensor is soluble in an organic solvent.

In some embodiments, the nanofibers have a diameter of less than or equal to about 1000 nm, more particularly 100-500 nm and in certain cases about 200 nm.

Additional aspects disclosed herein relate to methods of detecting an analyte. In certain aspects, the analyte is detected in a tissue of a subject. In these aspects, the methods comprise implanting a plurality of sensor matrices in the tissue. Each matrix comprises: i) a nanofiber, and ii) one or more sensors, each sensor matrix comprising nanofibers and one or more fluorescent sensor components, wherein the one or more sensor components detect an analyte, wherein the device is oblong with a surface area to volume ratio of at least 100 $mm^{-1}$ with a width of about 200 nm to about 500 nm and a length being greater than the width. Furthermore, the methods comprise contacting the plurality of sensor matrices with the analyte and detecting the analyte in the tissue.

In certain embodiments, the analyte is selected from the group consisting of electrolytes, proteases, hormones, steroids, small molecules, drugs, and saccharides. In other embodiments, the core further comprises a polymer. In other embodiments, the nanofiber includes the sensor. In particular embodiments, the nanofiber comprises a biocompatible polymer. In more particular embodiments, the nanofiber comprises a core and shell, wherein the sensor is present in at least one of the core and shell.

In certain embodiments, the core comprises one or more polymers selected from the group consisting of polyvinyl chloride, polylactic co-glycolic acid, methacrylate, and polycaprolactone.

In particular embodiments, detecting the analyte comprises (i) exciting one or more fluorescent sensors in the plurality of sensor matrices with an excitation energy emission from an energy emission device and (ii) detecting fluorescent energy emitted by the one or more fluorescent sensors in the plurality of sensor matrices.

In further embodiments, the energy emission device is a handheld device. In still more embodiments, the nanofiber has a diameter of less than or equal to about 1000 nm.

In some embodiments, the core and/or shell further comprises a plasticizer.

In certain embodiments, implanting a plurality of sensor matrices comprises injecting the plurality of devices into the tissue. In particular embodiments, the tissue is selected from the group consisting of epidermal, muscular, ocular, endothelial In certain embodiments, the analyte is selected from the group consisting of electrolytes, proteases, hormones, steroids, small molecules, drugs, and saccharides.

In certain embodiments, the nanofiber comprises one or more polymers selected from the group consisting of polyvinyl chloride, polylactic co-glycolic acid, methacrylate, and polycaprolactone In other embodiments, a method of detecting an analyte is disclosed. The method includes providing a plurality of sensor matrices, each sensor matrix comprising nanofibers and one or more sensor components, wherein the one or more sensor components detect an analyte, and the nanofiber comprises a coaxial core and shell with at least one of the sensor components in the shell; contacting the plurality of sensor matrices with the analyte; and detecting the analyte in the tissue of the subject. In some cases, the analyte may be detected using fluorescence or photoacoustic imaging.

DESCRIPTION OF THE FIGURES

The following figures are presented for the purpose of illustration only, and are not intended to be limiting:

FIG. 1 shows boronic acids incorporated into glucose-sensitive sensors.

FIG. 5 shows electrospun glucose-sensitive scaffolds.

FIG. 8 illustrates fluorescence measurements of glucose-sensitive nanoparticles and nanofiber scaffolds over time in vivo. The average normalized total radiant efficiency of glucose-sensitive (A) nanoparticles and (B) nanofiber scaffolds both in vivo (○) and in vitro control (■) were plotted over time. The normalized in vivo average for nanoparticles and nanofiber scaffolds was calculated across 3 different mice with $n_{nanoparticles}=8$ and $n_{nanofiber\ scaffolds}=6$ injection spots. Similarly, the normalized in vitro average was calculated from $n_{nanoparticles}=8$ and $n_{nanofiber\ scaffolds}=7$. Error bars represent standard deviations.

FIG. 9 illustrates methods for making injectable nanofibers. FIG. 9A shows nanofibers being injected as whole scaffolds using an indwelling needle assembly and FIG. 9B shows that nanofibers can be sonicated to form "whiskers" that can be injected like nanosensors.

FIG. 12 B shows the response to chloride for nanosensors electrospun into gelatin fibers.

FIG. 14 illustrates the phosphorescence emission characteristics of oxygen-sensitive dye.

FIG. 15 illustrates coaxial electrospinning of nanofibers.

FIG. 20A is a confocal image of scaffolds with cells grown on them (overlay of experimental and reference dyes), FIG. 20B presents fluorescent reader images of scaffolds, FIG. 20C shows the response with Meg01 cells, and FIG. 20D shows the response with T33 cells.

FIG. 21 presents a comparison of PVC-DOS nanosensors electrospun into a collagen fiber matrix (NS Fibers) with coaxially electrospun fibers.

DETAILED DESCRIPTION OF THE INVENTION

1. Sensor Matrices

Figures 1A, 1B:
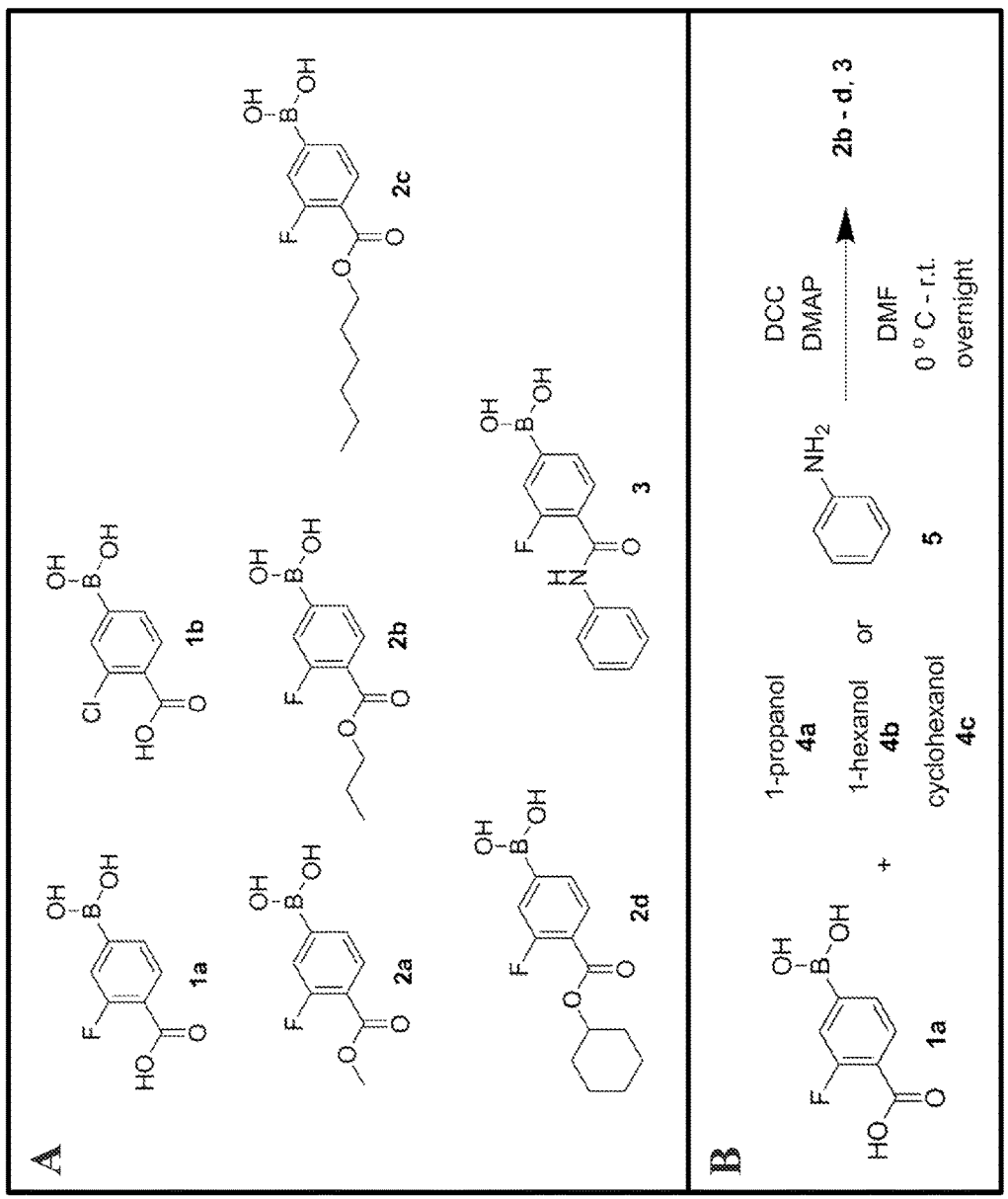
FIG. 1A provides the structures and FIG. 1B provides synthesis of boronic acids with different alkyl chain lengths and ring structures.

The patent and scientific literature referred to herein establishes knowledge that is available to those of skill in the art. The issued US patents, allowed applications, published foreign applications, GenBank accession numbers, and references that are cited herein are hereby incorporated by reference to the same extent as if each was specifically and individually indicated to be incorporated by reference.

The term "nanofiber" is used herein to refer to materials that are in the form of continuous filaments or discrete elongated pieces of material, and that typically have diameters of less than or equal to 1000 nanometers. In this regard, the term "nanofiber scaffold" is used herein to refer to the arrangement of such nanofibers into a supporting framework that can then be used to support cells or other additional materials. Various methods known to those of ordinary skill in the art can be used to produce nanofibers, including, but not limited to, interfacial polymerization and electrospinning.

In accordance with one aspect, analyte-sensitive nanofibers and scaffolds are prepared using electrospinning Electrospinning is a high rate manufacturing technique that can be used to produce fibrous scaffolds, which have high surface area to volume ratio, high porosities, and fibers with diameters in the nanometer to micron range. These characteristics are beneficial in sensor design because they shorten response times and enhance sensitivity. The scaffolds can be composed of a combination of plasticizers, polymers, and sensing components. Within the polymeric scaffold, traditional optode sensing components may be encapsulated or embedded in the nanofibers. Fibrous scaffolds may also be fabricated with any combination of polymers, plasticizers, coatings, stabilizers, and sensor components. Alternative constructions for the scaffolds also include core-shell fibers and injectable scaffolds.

For example, in some embodiments, electrospinning techniques can be used to generate nanofibers from a variety of materials, including polymers, composites, and ceramics. Typically, such electrospinning techniques make use of a high-voltage power supply, a spinneret (e.g., a hypodermic needle), and an electrically conductive collector (e.g., aluminum foil). To perform the electrospinning process using these materials, an electrospinning liquid (i.e., a melt or solution of the desired materials that will be used to form the nanofibers) is generally first loaded into a syringe and is then fed at a specific rate set by a syringe pump. In some cases, a well-controlled environment (e.g., humidity, temperature, and atmosphere) can be used to achieve a smooth, reproducible operation of electrospinning.

As the liquid is fed by the syringe pump with a sufficiently high voltage, the repulsion between the charges immobilized on the surface of the resulting liquid droplet overcomes the confinement of surface tension and induces the ejection of a liquid jet from the orifice. The charged jet then goes through a whipping and stretching process, and subsequently results in the formation of uniform nanofibers. Further, as the jet is stretched and the solvent is evaporated, the diameters of the fibers can then be continuously reduced to a scale as small as tens of nanometers and, under the influence of an electrical field, the nanofibers can subsequently be forced to travel towards a grounded collector, onto which they are typically deposited as a non-woven mat. In some embodiments, due to the high ratio of surface area to volume and the one-dimensional morphology, electrospun nanofibers can mimic the architecture of the extracellular matrix.

Furthermore, in some embodiments, the nanofibers themselves can include various secondary structures, including, but not limited to, microwells, core-shell structures, hollow structures, porous structures, and the like.

In some embodiments of the presently-disclosed subject matter, the nanofibers that are electrospun are comprised of a biodegradable polymer. The term "biodegradable" as used herein is intended to describe materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, oxidation, enzymatic processes, phagocytosis, or other processes.

Such biodegradable polymers are known to those of ordinary skill in the art and include, but are not limited to, synthetic polymers, natural polymers, blends of synthetic and natural polymers, inorganic materials, and the like. In some embodiments, the nanofibers are comprised of polycaprolactone. In some embodiments, blends of polymers are utilized to form the nanofibers to improve their biocompatibility as well as their mechanical, physical, and chemical properties. Regardless of the particular polymer used to produce the nanofibers, once the nanofibers have been created by the electrospinning process, the nanofibers can be assembled into a nanofiber scaffold or divided into nanowhiskers. Numerous methods of assembling nanofiber scaffolds and forming nanowhiskers can, of course, be used in accordance with the presently-disclosed subject matter. Nanowhiskers may have an average length of about 1 μm to about 500 μm, more particularly from about 1 to 10 μm and in other cases from about 400 to 500 μm and yet in other cases from about 100 to 200 μm.

In certain embodiments, the polymer can be biocompatible, such that the nanofiber formed from the polymer can be suitable for use in a variety of biological applications. "Biocompatible" and "biologically compatible", as used herein, generally refer to polymers that are, along with any metabolites or degradation products thereof, generally nontoxic to cells and tissues, and which do not cause any significant adverse effects to cells and tissues when introduced to the cells or tissues and when cells and tissues are incubated (e.g., cultured) in their presence. In some embodiments, only the shell polymer is biocompatible.

Examples of suitable polymers include, but are not limited to, polyolefins; polyethers; polyacrylates; polyesters; polyamides; polyimides; polysulfones; polysiloxanes; polyurethanes; polynitriles; polycarbonates; polyphosphazines; polyvinyl homopolymers and copolymers, such as poly (vinyl chlorides), poly vinyl butyrals), and poly(vinyl alcohols); poly(dienes); fluoropolymers such as polytetrafluoroethylene (PTFE); copolymers thereof, and blends thereof.

In some cases, the polymer can comprise polydimethylsiloxane (PDMS), polyethersulfone (PES), polystyrene (PS), polyvinyl chloride (PVC), polymethyl (meth)acrylate (PMMA), copolymers thereof, and blends thereof. In certain embodiments, the polymer can comprise PES, PDMS, or combinations thereof.

In some embodiments, the polymer can comprise an aliphatic polyester. For example, the polymer can be selected from the group consisting of poly(lactide), poly (glycolide), poly(lactide-co-glycolide), poly(caprolactone), copolymers thereof, and blends thereof. In certain embodiments, the polymer can comprise polycaprolactone (PCL).

In certain embodiments, the materials used to produce the nanofibers may be selected from those set forth in the following table, where the typical solvents and representative concentrations are exemplary only and not meant to be limiting in any way:

TABLE 1

Exemplary Materials for Electrospinning.

| Polymer | Typical Solvent | Representative Concentration |
|---|---|---|
| Polylactic acid, PLA | Dichloromethane | 5 wt. % |
| Polyethylene-co-vinyl acetate, PEVA | | 14 wt. % |
| PEVA/PLA = 50/50 | | 14 wt. % |
| Polyethylene oxide, PEO | Distilled water | 4-10 wt. % |
| Collagen-PEO | Hydrochloric acid | 1-2 wt % |
| Silk-like polymer with fibronectin functionality | Formic acid | 0.8-16.2 wt. % |
| Polyvinylcarbazole | Dichlormethane | 7.5 wt. % |
| polyacrylic acid-polypyrene methanol, PAA-PM | Dimethyl formamide | |
| Silk/PEO blend | Silk aqueous solutions | 4.8-8.8 wt. % |
| Cellulose acetate, CA | Acetone, acetic acid, dimethylacetamide | 12.5-20% |
| Chitosan | Acetic acid | |
| Fibrinogen | Hexafluoro-2-propanol | |
| Mixture of PAA-PM (polyacrylic acid - poly (pyrene methanol)) and polyurethane | Dimethylformamide | 26 wt. % |
| PLGA | Tetrahydrofuran:dimethylformamide (1:1) | 1 g/20 ml |
| Collagen | Hexafluoro-2-propanol | |
| poly(ethylene-co-vinyl alcohol) | Isopropanol/water: 70/30 (% v/v) | 2.5-20% w/v |

Described herein are studies which demonstrate how electrospinning of fibers can be used to produce scaffolds or nanowhiskers useful for maintaining the sensor devices described herein in a desired location. Furthermore, variation of the parameters associated with electrospinning can be used to control the fiber characteristics to suit a particular situation.

A number of parameters can be used to control the properties of the fibers formed using electrospinning. The following parameters are mentioned as particularly useful in controlling the collected fibers:

1. Solvent
2. Molecular weight of polymer
3. Concentration of polymer-solvent solution
4. Applied voltage
5. Tip to collector distance
6. Flow rate of polymer-solvent solution These and other parameters are discussed in more detail below.

Suitable solvents include, but are not limited to, acetone, chloroform, dichloromethane (DCM), tetrahydrofuran (THF) and hexafluoroisopropanol (HFIP).

The polymers useful herein typically are not particularly limited by molecular weight. The polymer solution forming the conducting fluid will preferably have a polymer concentration in the range of about 1 to about 80 wt %, more preferably about 10 to about 60 wt %. The conducting fluid will preferably have a viscosity in the range of about 50 to about 2000 mPa-s, more preferably about 200 to about 700 mPa-s.

In particular embodiments, the nanofiber further comprises a plasticizer. The plasticizers are additives that increase the plasticity or fluidity of the nanofiber. Any biocompatible plasticizer that does not affect the one or more sensors ability to detect an analyte can be used. In certain embodiments, the nanofiber comprises about 25% to 75% plasticizer. In other embodiments, the plasticizer is about 33% to 66% of the total material.

As used herein, the term "sensing agent" or "sensor" means a compound, nanoparticle, or substance that emits light when contacted by light or electromagnetic radiation. For a one-component system, the system may include a fluorescent or phosphorescent dye that is quenched, as in the case of oxygen detection. Typically sensors useful herein may have three components: ionophore (no optical properties, binds to analyte), chromoionophore (flureoscent or color change dep on pH), and an ionic additive that sets up a charge neutrality in the plasticized polymer matrix. In accordance with certain systems, an enzyme is added by starting with a "standard" one or three component sensor and adding an enzyme to it to detect a larger molecule. That analyte is degraded, and a sensor particle is used to detect the byproduct of the reaction (such as oxygen or pH change).

Such sensor matrices advantageously allow the sensors to remain at site of administration, while allowing the sensors to detect rapidly analytes. Generally, any structure that provides a high aspect ratio for the device is particularly useful. By "high aspect ratio," it is meant that the structures disclosed herein have lengths that are longer than their widths. In accordance with certain aspects, the surface area to volume ratio is at least 100 mm$^{-1}$ or in some cases at least 1000 mm$^{-1}$.

The sensor matrix has a length that is greater than the diameter. For instance, the sensor matrix can have a length of about 40 μm to about 60 μm and a diameter of between about 200 nm to about 500 nm. In still other embodiments, the sensor matrix has a diameter of about 500 nm to about 1000 nm.

In certain aspects, the sensor matrix comprises sensors that are capable of binding to an analyte. In certain aspects, the nanofiber comprises one or more sensors configured to bind to an analyte. The sensors can bind electrolytes, proteases, hormones, steroids, small molecules, drugs, and saccharides. The sensors disclosed herein can bind to sodium, potassium, bicarbonate, or other electrolytes. The sensors can also bind to magnesium, calcium, or other salts. The sensors can be to transition metals such as iron, manganese, nickel, and cobalt. The sensors can also bind to hormones such as testosterone, estrogen, or other hormones. The sensors can also bind to cholesterol and other cholesteryl-based structures. The sensors can further bind to small molecules having molecular weight of less than 1 kD. In certain embodiments, the small molecules can have a molecular weight of less than 2 kD.

In addition, the sensors disclosed herein can be fluorescent sensors. In such embodiments, the fluorescent sensors can be excited by any wavelength of light between 400 nm to 800 nm. In certain embodiments, the excitation wavelength of light is between 450 nm to 700 nm. Other sensors can be based on absorbance, phosphorescence and photoacoustic imaging.

2. Methods of Making Fibrous Sensor Matricess

Aspects disclosed herein include methods of making sensor matrices. In certain embodiments, the methods comprise preparing optode solutions containing a polymer, sensing elements, and typically a plasticizer and reference dye (optimized to the system at hand). The relative concentrations of the sensing elements will determine the response of the sensor to the analyte. A small amount of coating polymer is added into a glass vial and air dried. The desired aqueous solution is then introduced to the vial and sonicated. While the solution is being sonicated, the optode material is mixed with a solvent and sonicated. Once sonication is complete, the nanosensor solution is pulled up into a syringe. The nanosensor solution is dispensed through a filter into a glass vial.

Optode solutions are made for the nanofiber core solution according to which analyte is to be tested. The nanofiber core/sheath solution comprises the proper amount of polymer in a solvent. The optode solution is then added and the solution is incubated at 37° C. and vortexed until polymer dissolves.

Optode solutions may be spun into nanofibers using a vertical electrospinning apparatus, such as an Inovenso Ne200 Nanospinner (Maslak, Istanbul). Nanosensor solutions are drawn into a syringe, which is then attached to a syringe pump set to an appropriate flow rate (rate dependent on polymer used). A voltage is applied to induce fiber formation onto glass cover slips attached to an aluminum foil-covered collector plate or glass cover slips attached to a rotating mandrel set at an appropriate speed (for aligned fibers or other configurations).

Coaxial electrospinning can be used to produce fibers with a surface shell and a polymer core. For coaxially-spun fibers, the core solution syringe can be attached to the inner bore of a concentric spinning headpiece and the sheath solution syringe can be attached to the outer bore.

Nanowhiskers can be formed by sonicating the nanofibers in glass vial with an appropriate solvent and then evaporating the solvent and washing the sonicated nanofibers with buffer.

3. Detecting Optode Sensors

Aspects disclosed herein include methods of detecting an analyte in a tissue of a subject. The method comprises implanting a plurality of sensor matrices in the tissue of a subject. The implanting can involve surgical implantation, injection into tissue, or administering to the surface of a tissue. Furthermore, the methods comprise detecting an analyte in the tissue. Exemplary tissues include epithelial tissues such as skin, endothelial tissues such as blood vessel walls, organ tissues, ocular tissues, muscle tissues, and mucosal tissues.

In embodiments in which the sensor matrices are administered to a subject, the sensor matrices can be administered in solutions that allow for administration of the sensor matrices to a site of interest. The only limitation on such solutions is that they must not interfere with the functioning of the sensor matrices.

In certain embodiments, the sensor matrices are tattooed onto the subject. Such tattooing has been disclosed previously in U.S. Appl. Pub. No. 2009/0155183 A1, incorporated by reference herein. In such embodiments, the intra- and extra-cellular sensor matrices reside under the tissue. In certain embodiments, popular, commercially available portable electronic devices with optical readers can be transformed into a diagnostic instrument that can also communicate with care providers and provide assistance in emergency cases.

In additional embodiments, the sensor matrices are biocompatible to prevent an immune response. The response can be specific to the concentration of the molecule or ion being measured. The response can be quantitatively measurable by the portable electronic imaging device.

Other aspects include methods of detecting an analytes comprising providing a plurality of devices into a sample. In these aspects, the optode sensors are provided to a sample isolated from a patient. For instance, the samples are isolated by biopsy or other minimally invasive means. The samples can also be isolated by surgical procedures. The isolated tissues can be processed using techniques known in the art to obtain a sample amenable to ELISA procedures or other fluorescent-based detection procedures.

Further embodiments entail providing or attaching sensor matrices into a well, such as on a multiwell plate, tubing, chip, membrane, or surface that contacts samples in which analytes are present. In these embodiments, the sensor matrices interact or bind to analytes. Subsequently, the sensor matrices that have interacted or bound to analytes will fluoresce when contacted with an excitation light. Thus, the sensing agents can detect one or more analytes that have passed across a surface. Methods of attaching polymers to solid supports such as microchips are known in the art, e.g., Hynd M, et al. Functionalized hydrogel surfaces for the patterning of multiple biomolecules. *Biomaterials*. (2007) 81:347-54, the disclosure of which is incorporated by reference.

Sensor matrices can be continuous monitoring agents in the disclosed methods. To be a continuous monitoring agent, the response time of the sensor matrices should be fast. The response time of the sensor is completely dependent on diffusion within the optode and decreases below seconds as the size decreases to microns (Bakker E, Balmann P, Pretsch E (1997) *Chem Rev* 97:3083-3132). Theoretical response times of the nanosensors and the sensor matrices can be estimated by solving the diffusion equation for a sphere (see, e.g., Crank J (2004) The Mathematics of Diffusion (Oxford Univ Press, New York), pp 69-104) and a rod (see, e.g., Crank J (2004) The Mathematics of Diffusion (Oxford Univ Press, New York), pp 69-104).

The response mechanism of the sensors to sodium has been previously explained (Bakker E, Balmann P, Pretsch E (1997) *Chem Rev* 97:3083-3132). Briefly, in accordance with one aspect, the optode comprises a plasticized polymer that creates a hydrophobic environment in which a pH sensitive fluorophore, an ionophore specific for sodium, and a charge neutrality molecule are contained. Selective uptake into the optode by the ionophore brings a positive charge into the polymer resulting in a loss of a hydrogen ion to balance the charge. This hydrogen ion loss changes the protonation state of the fluorophores and thus the optical properties of the optode. The optical response of nanosensors and sensor matrices to sodium was determined with a plate reader.

Additionally, sensor matrices can be in vivo monitoring agents. For continuous in vivo monitoring, the diffusion of the sensors should be minimized. The diffusion coefficient, D, can be calculated using the Stokes-Einstein equation $D=kT/6\pi\eta R_h$, where k is Boltzmann's constant and $\eta$ is the viscosity of water. The hydration radius ($R_h$) of the sensor matrices can be found from the radius of gyration ($R_g$) (30), here $R_g=1.732\ R_h$. The $R_g$ of a cylinder depends on the length and radius [$R_g=L^2/12+r^2/2^{1/2}$], where L is the length and r is the radius. For aspect ratios $L/r\gg1$ the radius of the optode sensing agent contributes little to $R_g$ and can be ignored in this case because L/r=400. For a length of 40 μm and a radius of 100 nm, the $R_h$ of the optode sensing agent is 6.67 μm. The surface-area-to-volume ratio of the optode sensing agent is 20 $\mu m^{-1}$, whereas the surface-area-to-volume ratio of a sphere with an Rh of 6.67 μm is 0.45 $\mu m^{-1}$. At smaller effective $R_h$, the surface-area-to-volume ratio is actually greater for spheres. However, once the effective $R_h$ is above 150 nm, the optode sensing agent structure provides an improved surface-to-volume ratio.

4. Detection Devices

As discussed above, the methods of detection can be utilized to cause excitation of the fluorescent molecules. In certain embodiments, the fluorescence emitted can be captured using devices useful in fluorescence imaging. For instance, the images of the fluorescence can be captured on a camera on a portable electronic device. Furthermore, the sensor matrices can be detected using standard ELISA techniques in vitro. In other embodiments, the sensor matrices are detected using devices known in the art. For instance, the IVIS Spectrum Imaging System (Caliper Lifesciences, Hopkinton, Mass.) is useful for in vivo detection of fluorescence.

In certain embodiments, the sensor matrices are detected using a portable electronic device converted into a handheld diagnostic device. An example of a portable electronic device converted to a handheld diagnostic agent is described in U.S. Patent Application Publication No. 2013/0197326, to Dubach et al., the contents of which are hereby incorporated by reference.

In particular embodiments, a kit is provided with the sensor matrices and reference agents for calibrating detection devices. The kits can comprise packaging that is fluorescent and can be used to calibrate the detection devices used to detect the fluorescent sensors. For instance, the kit houses two compartments of sensor matrices at known analyte concentrations. When a fluorescent image of the packaging is taken, the fluorescence intensity can be measured. Because the analyte concentration is known, and the calibration curve of this specific lot of sensors has been determined based on a QR code, the intensity measurement can be used to adjust the calibration curve to the particular device. In some embodiments, two measurements at known concentrations of analyte—such as sodium—can allow a software application to set the calibrated response to the correct fluorescence ration. Such software calibration is known in the art.

This approach will completely calibrate the sensors at each measurement point to eliminate drift in sensor functionality or other measurement artifacts. The intensities at each measurement will be recorded by the software application and alert patient.

The fluorescent image of the sensors in the packaging can be used to measure the fluorescence intensity of the sensing agents; this calibrates the tissue of the subject. By taking an image of these sensors, both before and after injection, a software program can determine how the tissue alters the fluorescence. This known alteration of the fluorescence can then be used to determine the correct analyte concentration from the fluorescence of the analyte sensors. This can be performed using the following equations:

$$Z = \frac{R_{Packaging}^{Reference}}{R_{Injected}^{Reference}}, R_{True}^{Na} = Z * R_{Measured}^{Na}$$

"Z" is a correction factor that is calculated by dividing the intensity "R" of the reference sensors in packaging by the value immediately after the sensors have been injected. The packaging value will be stored for the lifetime of the sensors and used to create a new "Z" at each reading. The true "R" of the sodium sensors will then be determined by multiplying "Z" by the measured "R" of the sodium sensors.

In medical diagnostic embodiments, a doctor or a patient is provided with a kit comprising the fluorescent sensors and a light-protective cover. After a light-protective cover has been removed the patient can take two images, one bright field and one fluorescent. The bright field image will allow the disclosed system to register the sensors by recognizing the QR code. A QR code is similar to a barcode and is an increasingly common way to relay information. The code will provide the lot number of the sensor matrices which can be used to determine expiration date and calibrated response of the devices. The optode sensing agent lot can be calibrated in the factory and this information can be transferred to the portable electronic device.

In further embodiments, reference sensors are injected into the tissue that will be imaged each time the analyte concentration is determined. Therefore, at each measurement the correction factor obtained from the fluorescence of these sensors will be adjusted. This can remove error that may occur from sensing agent degradation, photobleaching, tissue autofluorescence or other biological or physical artifacts when sodium concentration is measured.

After the doctor or patient has taken images of the packaging, the sensors will be injected into the tissue or surgically implanted into the tissue directly. One of the compartments containing sensor matrices is administered to the tissue. In certain embodiments, reference sensors are administered to another position in the tissue. There are several minimally-invasive injection technologies that are FDA-approved and available on the market. These injection technologies are mainly designed for drug delivery devices or vaccine administration, but may be adapted for sensor delivery into the intradermal space. For example, in March 2011 the FDA cleared the first intradermal needleless injection system by PharmaJet® for vaccine delivery. These injection systems can delivery up to 100 µl of solution to the intradermal space using a high pressure system. Microneedle delivery systems can also be used to deliver sensors into the intradermal space without triggering the nerve fibers. After the two spots have been injected, a simple mark from a stamp in the packaging will indicate where the injections have been made as well as the orientation of the two spots.

In certain embodiments, a patient monitors analyte concentrations. Any time the patient wants to measure his or her analyte levels, the patient takes an image of the injection spot. This can provide an accurate measurement in real time that is pain free. After the sensors have been injected they can last for one week before they need to be replaced. At some point after a week, the sensors will begin to biodegrade and be removed naturally by the body. Removal can occur by renal elimination and sloughing off of sensor material when the dermis layer of the skin is replaced. To replace the sensors the patient simply uses a new package of sensors, takes the initial images, and injects the sensors in a different spot in their skin. There will be no permanent effects from the sensors so the same spot could eventually be used again.

In an illustrative embodiment, the fluorescent sensors have multiple fluorescent excitation and emission wavelengths that can be used to determine fluorescent intensity. To achieve quantitative and accurate measurements, however, a ratio of two wavelengths must be used. This eliminates the dependency of the calculated sodium concentration on the number of sensors present, accounts for skin inhomogeneity, sensor injection depth, and possible photobleaching. Two emission wavelengths can be created by exciting the chromoionophore, for example, at 476 nm and collecting emission, for example, at the 570 nm and 670 nm peaks.

EXAMPLES

A. General Procedures

Nanosensor Fabrication:

Materials—Polyvinylchloride (PVC), tetrahydrofuran (THF), bis (2-ethylhexyl) sebacate (DOS), additive to detect analyte of interest, Chromoionophore (specific to the analyte), ionophore (specific to analyte), reference dye (specific to analyte), 1,2-Distearoyl-sn-Glycero-3-Phosphoethanolamine-N-[Methoxy(Polyethyleneglycol)-550] in chloroform (PEG-lipid), dichloromethane (DCM).

Method—Optode solutions containing a polymer (PVC), sensing elements, and plasticizer (DOS) and reference dye (optimized to the system at hand) are made. The relative concentrations of the sensing elements will determine the response of the sensor to the analyte. Pipette 50 µl of 25 mg/ml PEG-lipid into a 4 dram glass vial and air dry. Add 4 ml of the desired aqueous solution to the vial with PEG-lipid. Place the vial on a laboratory jack underneath the sonicating tip and raise the vial until the tip is about 7 mm deep in the solution and sonicate at 20% amplitude for 30 seconds. While the solution is being sonicated, mix 50 µl of the optode material with 50 µl of DCM in a 100 uL PCR tube. Mix with the pipette to ensure even mixing. Adjust the sonicator control to ~2 mm deep in the solution and to sonicate for 3 minutes. Start the sonication and add the optode mixture solution immediately to the vial by immersing the pipette tip into the solution and dispensing the 200 µl of solution in one quick, even injection. Once sonication is complete, pull up the nanosensor solution into a 5 ml syringe. Attach a 0.8 µm syringe filter and dispense the nanosensor solution into a glass vial with screw top cap.

Examples of Potential Analytes for Nanofibers

TABLE 2

| Target Analyte | Sensing Mechanism | Recommended Enzyme Name | Systematic Name of Enzyme | Reaction |
| --- | --- | --- | --- | --- |
| prostaglandin A1 | O2, ROS | leukotriene-B4 20-monooxygenase | (6Z,8E,10E,14Z)-(5S,12R)-5,12-dihydroxyicosa-6,8,10,14-tetraenoate, NADPH:oxygen oxidoreductase (20-hydroxylating) | prostaglandin A1 + NADPH + O2 --> 20-hydroxy-prostaglandin A1 + NADP+ + H2O |
| 15-ketoprostaglandin E2 | ROS | 15-oxoprostaglandin 13-oxidase | 11alpha-hydroxy-9,15-dioxoprostanoate:NAD(P)+ Delta13-oxidoreductase | 15-ketoprostaglandin E2 + NADPH --> 13,14-dihydro-15-keto-prostaglandin E2 + NADP+ |

TABLE 2-continued

| Target Analyte | Sensing Mechanism | Recommended Enzyme Name | Systematic Name of Enzyme | Reaction |
|---|---|---|---|---|
| (6E,8Z,11Z,14Z)-(5S)-hydroperoxyicosa-6,8,11,14-tetraenoate | O2 | arachidonate 5-lipoxygenase | arachidonate:oxygen 5-oxidoreductase | (6E,8Z,11Z,14Z)-(5S)-hydroperoxyicosa-6,8,11,14-tetraenoate + O2 --> leukotriene A4 |
| leukotriene B4 | O2 | leukotriene-B4 20-monooxygenase | (6Z,8E,10E,14Z)-(5S,12R)-5,12-dihydroxicosa-6,8,10,14-tetraenoate, NADPH:oxygen oxidoreductase (20-hydroxylating) | leukotriene B4 + NADPH + O2 --> 20-hydroxy-leukotriene B4 + NADP+ + H2O |
| leukotriene B4 | O2 | leukotriene-B4 20-monooxygenase | (6Z,8E,10E,14Z)-(5S,12R)-5,12-dihydroxicosa-6,8,10,14-tetraenoate, NADPH:oxygen oxidoreductase (20-hydroxylating) | leukotriene B4 + NADPH + H+ + O2 --> (6Z,8E,10E,14Z)-(5S,12R)-5,12,20-trihydroxyicosa-6,8,10,14-tetraenoate + NADP+ + H2O |
| Cholesterol | O2 | cholesterol oxidase | cholesterol oxidase | Cholesterol + O2 → cholest-5-en-3-one + H2O2 |
| (12S)hydroperoxy-5,8-cis-10-trans-13-cis-eicosatetraenoic acid (12S) HpETE | O2 | Arachidonate 5-lipoxygenase | arachidonate:oxygen 5-oxidoreductase | (12S)hydroperoxy-5,8-cis-10-trans-13-cis-eicosatetraenoic acid (12(S) HpETE) + O2 --> (5S,12S)-dihydroperoxy-5,8-cis-10-trans-13-cis-eicosatetraenoic acid (5(S),12(S) DiHETE) |
| arachidonic acid | O2 | Arachidonate 8-lipoxygenase | arachidonate:oxygen 8-oxidoreductase | arachidonic acid + O2 --> (8R)-8-hydroperoxy-5,9,11,14-eicosatetraenoic acid |
| arachidonate | O2 | Arachidonate 12-lipoxygenase | arachidonate:oxygen 12-oxidoreductase | arachidonate + O2 --> (5Z,8Z,10E,14Z)-(12S)-12-hydroperoxyicosa-5,8,10,14-tetraenoate (12(S)-HpETE) |
| arachidonic acid | O2 | Leukotriene A synthase | | 2 arachidonic acid + 2 O2 --> 8-hydroxy,9-oxo-eicosa-5Z,11Z,14Z-trienoic acid + 9-oxo-[8,12-cis]-prosta-5Z,10,14Z-trienoic acid + H2O |
| arachidonate | pH and O2 | Arachidonate 15-lipoxygenase | arachidonate:oxygen 15-oxidoreductase | 2 arachidonate + 2 O2 + H+ --> (5Z,8Z,11Z,13E)-(15S)-15-hydroperoxyeicosa-5,8,11,13-tetraenoate + (5Z,8Z,11Z,13E)-(15S)-15-hydroxyeicosa-5,8,11,13-tetraenoate + H2O |
| prostaglandin D2 | pH | prostaglandin-F synthase | (5Z,13E)-(15S)-9alpha,11alpha,15-trihydroxyprosta-5,13-dienoate:NADP+ 11-oxidoreductase | prostaglandin D2 + NADPH + H+ --> prostaglandin 9alpha,11beta-F2 + NADP+ |
| prostaglandin H2 | pH | prostaglandin-F synthase | (5Z,13E)-(15S)-9alpha,11alpha,15-trihydroxyprosta-5,13-dienoate:NADP+ 11-oxidoreductase | prostaglandin H2 + NADPH + H+ --> prostaglandin F2alpha + NADP+ |
| prostaglandin E2 | pH | prostaglandin-E2 9-reductase | (5Z,13E)-(15S)-9alpha,11alpha,15-trihydroxyprosta-5,13-dienoate:NADP+ 9-oxidoreductase | prostaglandin E2 + NADPH + H+ --> prostaglandin F2alpha + NADP+ |
| prostaglandin A2 | pH | 15-hydroxyprostaglandin-D dehydrogenase | (5Z,13E)-(15S)-9alpha,15-dihydroxy-11-oxoprosta-5,13-dienoate:NADP+ 15-oxidoreductase | prostaglandin A2 + NADP+ --> 15-ketoprostaglandin A2 + NADPH + H+ |
| aldehydes | pH | aldehyde dehydrogenase | aryl-aldehyde dehydrogenases | aldehyde + NAD+ + H2O → a carboxylate + NADH + H+ |
| 11beta-hydroxysteroid | pH | 11beta-hydroxysteroid dehydrogenase | 7-alpha-hydroxycholesterol dehydrogenase | 11beta-hydroxysteroid + NAD+ → an 11-oxosteroid + NADH + H+ |
| UDP-alpha-D-galactose | Glucose | lactose synthase | alpha-lactalbumin | UDP-alpha-D-galactose + D-glucose → UDP + lactose |

1. Incorporation of Nanosensors into Nanofibers:

Materials—Optode for analyte to be tested, polymer (from Table 1), 1,1,1,3,3,3-Hexafluoro-2-propanol (HFIP)

Method—Optode solutions are made for the nanofiber core solution according to which analyte is to be tested. The nanofiber sheath solution consisting of 11% (w/v) polymer in HFIP is prepared by dissolving the proper amount of polymer needed to achieve 11% w/v in the desired final volume of HFIP (90% v/v). 10% of the Optode solution is then added and the solution is incubated at 37° C. and vortexed until polymer dissolves.

Optode solutions are spun into nanofibers using a vertical electrospinning apparatus in an Inovenso Ne200 Nanospinner (Maslak, Istanbul). Nanosensor solutions are drawn into a 5-mL syringe, which is then attached to a syringe pump set to a flow rate of 4 mL/hr (rate dependent on polymer used). For standard fiber electrospinning, the syringe containing the Nanosensors was connected to a copper headpiece by plastic tubing. A voltage of 15 kV was applied to induce fiber formation onto 5 mm glass cover slips attached to an aluminum foil-covered collector plate or 25 mm glass cover slips attached to a rotating mandrel set at a speed of 2 rotations/second (for aligned fibers).

2a. Core Sheath Nanofiber Fabrication:

Methods—Coaxial electrospinning produces fibers with a surface shell and a polymer core. For coaxially-spun fibers, the core solution syringe was attached to the inner bore of a concentric spinning headpiece and the sheath solution syringe was attached to the outer bore.

2b. Nano Whisker Fabrication:

Method—Sonicate the nanofibers in glass vial with 2-propanol for 5 min or more. Evaporate the solvent and wash the sonicated nanofibers for three times with buffer.

Conjugation of Enzyme onto Polymer Core-Collagen Sheath Nanofibers

Materials—Traut's reagent, 5,5'-dithio-bis-(2-nitrobenzoic acid) (DTNB, Ellman's reagent), β-mercaptoethanol (β-ME), enzyme (specific to analyte), phosphate-buffered saline (PBS), ethylenediaminetetraacetic acid (EDTA)

Method—Traut's reagent is dissolved in PBS (with 4 mM EDTA) to prepare different concentrations by serial dilution. The scaffold is immersed in 100 μl of Traut's reagent solution at different concentrations at 4° C. for 12 h. After washing, the scaffold is immersed in 200 μl of 0.1 mg/ml DTNB. The scaffold is then incubated for 15 min at RT, after which 100 μl is transferred to a new plate. β-ME, at a range of concentrations prepared by serial dilution, is reacted with 200 μl of 0.1 mg/ml DTNB for 15 min at RT and 100 μl of the reacted solutions are transferred to the other half of the same plate used to obtain the standard concentration curve. The samples are analyzed with a plate reader at 405 nm to determine the approximate amount of sulfhydryl groups.

For the cross-linking group the scaffold is immersed in 2.5 mg/ml Traut's reagent solution. After incubation at 4° C. for 12 h the samples are washed in PBS (with 4 mM EDTA) before use. Enzyme, in a range of concentrations prepared by serial dilution, is reacted with a 50-fold molar excess of sulfo-SMCC for 5 min at RT. The collagen-SH scaffold is immersed in 100 μl of the enzyme solution for 1 h at 4° C., then the scaffolds are washed three times in PBS on a shaker in order to remove unbound MAO and the extra cross-linking agent.

Incorporation of Quantum Dots into Nanofibers

Materials—Bis(2-ethylhexyl) sebacate (DOS), chromoionophore II (CHII, 9-Dimethylamino-5-[4-(16-butyl-2,14-dioxo-3,15-dioxaeicosyl)phenylimino]benzo[a]phenoxazine, ETH 2439), potassium ionophore III (KI3, 2-Dodecyl-2-methyl-1,3-propanediyl bis[N-[5'-nitro(benzo-15-crown-5)-4'-yl]carbamate]), Sodium tetrakis[3,5-bis(trifluoromethyl)phenyl]borate (NaBARF), 4-(2-Hydroxyethyl)piperazine-1-ethanesulfonic acid (HEPES), sodium chloride (NaCl), 90,000 MW poly(vinyl chloride) (PVC), dichloromethane (DCM) and tetrahydrofuran (THF) were purchased from Sigma-Aldrich. Quantum dots were purchased from NN-Labs (emission peak 640 nm, CZ640) and Cytodiagnostics (emission peak 490 nm, FN-490). Tris Base was purchased from Fisher BioReagents. Spectra/Por in vivo micro-dialysis hollow fibers (inner diameter 200 μm; outer diameter 280 μm, MWCO 13 kD) were purchased from Spectrum Labs, Inc. 1,2-distearoyl-sn-glycero-3-phosphoethanolamine-N-[methoxy(polyethylene glycol)-550] (ammonium salt) (DSPE-mPEG550) was purchased from Avanti Polar Lipids, Inc.

Method—Quantum dots are flocculated from chloroform by mixing as-received stocks in anhydrous methanol at a volume ratio of 4:1 MeOH:CHCl$_3$ and centrifuging for 5 minutes at 5000×g. After repeating the wash and centrifugation steps three times, the quantum dots are resuspended in THF and their concentration is determined based on absorbance. The sensing components KI$_3$ (4 μmol, 2 mg), CHM (1.36 μmol, 1 mg), and NaTFPB (13.5 μmol, 12 mg) are reconstituted separately with THF and combined in a 2 mL glass vial so that the total THF volume is 300 μL. DOS (428 μmol, 200 μL) is then added to the sensing components and vortexed briefly to homogenize the mixture. Just prior to nanosensor fabrication, 5 mg of DSPE-mPEG 550 is dried in a glass scintillation vial and reconstituted in 400 μL of DCM. 50 μL of the optode stock, 189 μg of QD490 and 182 μg of QD640 are added to the mixture. 4 mL of aqueous buffer (10 mM HEPES buffer; 6 mM tris base) is then added and the mixture is sonicated for 1 minute with a Branson digital sonifier (S-450D) at 10% intensity with a ⅛" diameter tip. After sonication, the organic solvents are removed using a rotavap (Buhle) for 10 minutes at room temperature. The resulting emulsion is filtered with a 100 nm syringe filter.

In Vitro Testing of Nanofibers

Method—Fibers on 5 mm glass cover slips were transferred to a 96-well plate. Calibration solutions of varying concentrations are made according to the analyte being tested and added to the wells and fluorescence readings are collected by a Molecular Devices SpectraMax M3 (Sunnyvale, Calif.).

Cell Growth on Nanofibers

Materials—HUVEC-EC cells from ATCC (Manassas, Va.), Ham's F12 medium, Penicillin/Streptomycin, and Fetal Bovine Serum (FBS) were purchased from HyClone (Logan, Utah), 0.25% Trypsin/EDTA, Endothelial Cell Growth Supplement (ECGS), Heparin sulfate, and acetylcholine (ACh) were purchased from Sigma (St. Louis, Mo.)

Method—HUVEC-EC cells are grown in Ham's F12 medium supplemented with 10% FBS, 1% Penicillin/Streptomycin, 0.1 mg mL-1 Heparin sulfate, and 30 μg mL-1 ECGS to ~90% confluency under conditions of 37° C. and 5% CO$_2$. The cells are then trypsinized using a 0.25% solution of trypsin/EDTA, centrifuged at 1500 rpm for 20 minutes, and resuspended in growth medium. Nanofober scaffolds on 25 mm glass slides are transferred to a 6-well plate. The scaffolds are sterilized in 70% ethanol for 15 minutes and incubated with growth medium. Cells are plated at a concentration of $3\times10^4$ cells $mL^{-1}$ and allowed to grow for 48 hours at 37° C. and 5% $CO_2$. Prior to imaging, the media was removed and replaced with PBS. Cells were then stimulated to produce NO by adding 0.1M acetylcholine solution. Images were collected by confocal microscopy as described.

In Vivo Testing of Nanofobers

Method—The mice used in this research are SKH1-E Nude mice from Charles River (Wilmington Mass.). Fluorescent imaging experiments are conducted using a Lumina II in vivo imaging system (IVIS). Animals were anesthetized with 2.25% isoflurane in oxygen and placed in the animal imager. The nanofibers are introduced into the animals (by injection or implantation, see below) and imaged with two channels. Baseline images are acquired for approximately 30 minutes, followed by an i.p. injection of 75 mg/kg analyte (experimental) or a matching volume of PBS (control). Images are acquired every minute for approximately one hour. All animals are sacrificed after experiments are completed. For data analysis of each experiment, a region of interest encompassing the injection area is selected and total fluorescent intensity for each channel is recorded. This data is then averaged together across three experimental animals and three control animals using linear interpolation to align time and intensity points before averaging.

8a. In Vivo Injection of Nanofibers:

Method—Anesthetize mouse. Wait until mice are sedated and do not respond to mild painful stimulus (pedal reflex). Place mouse in prone position on a heated pad. A fibrous scaffold will be loaded into the outer needle (≥23 gauge) of a modified indwelling needle assembly. The inner needle of the assembly will be flattened or rounded in order to serve the function of a plunger. The assembly will be inserted to the subcutaneous space of the injection site. The outer needle will be removed while holding the inner needle steady to prevent the scaffold from being extracted with the outer needle, leaving it behind in the injection site. This procedure will be repeated for multiple injection sites on the animal (along both sides of the back or along the centerline of the back)

8b. In Vivo Injection of Nano Whiskers

Method—Anesthetize mouse. Wait until mice are sedated and do not respond to mild painful stimulus (pedal reflex). Place mouse in prone position on a heated pad. Sonicate the nanofibers in glass vial with 2-propanol for 5 min or more. Vaporate the solvent and wash the sonicated nanofibers for three times with buffer. After the sonicated nanofibers are washed, we could use disposable and sterile syringes and needles to do the injection the same as with hollow fibers as noted above.

8c. In Vivo Implantation of Nanofibers

Anesthetize mouse. Wait until mice are sedated and do not respond to mild painful stimulus (pedal reflex). Place mouse in prone position on a heated pad. If necessary, remove hair by shaving and then using depilatory cream. Wipe skin with Betadine and then alcohol three times sequentially. Drape animal. Holding the skin between the hip joints with forceps, make a small incision (~5 mm) perpendicular to the long axis using scissors in the other hand. Place closed scissors into the incision site and open scissors making a pocket in the skin. Cut the skin orthogonally ~5-10 mm from each edge of the incision site and flip the skin flap exposing the subcutaneous space. Place the sterilized scaffold onto the subcutaneous tissue and fold the skin flap back over.

Repeat above procedure to place up to two more scaffolds along the centerline. Use an autoclip applier to close the wound with an autoclip or close the wound with nylon sutures. If imaging is to be done immediately following implantation, transfer anesthetized animal to imager. If imaging is to take place in the future, remove from anesthesia and monitor until ambulatory.

Example 1: Glucose-Sensitive Nanofiber Scaffolds

Materials and Methods

Materials: Carboxylated poly(vinyl chloride) (>97% GC) (PVC-COOH), bis-(2-ethylhexyl)sebacate (DOS), polycaprolactone ($M_n$ 70,000-90,000) (PCL), tridodecylmethylammonium chloride (TDMAC), alizarin, 4-carboxy-3-fluorophenylboronic acid (1), 3-fluoro-4-methoxycarbonylphenylboronic acid (2a), D-(+)-glucose, tetrahydrofuran (≥99.9%) (THF), dicyclohexylcarbodiimide solution (60% w/v in xylene) (DCC), N-hydroxysuccinimide (NHS), aniline(≥99.5%), 1-propanol (anhydrous, 99.7%), 1-butanol (HPLC, 99.7%), 1-hexanol (98%), cyclohexanol (99%), sodium sulfate (anhydrous, ≥99.9%), sodium chloride, ethyl acetate (anhydrous, 99.8%), hexane (anhydrous, 99.5%), N,N'-dimethylformamide (DMF) and N,N'-dimethylaminopyridine (DMAP) were purchased from Sigma Aldrich (St Louis, Mo., USA). Octylboronic acid (>97%) and Citroflex A-6 were acquired from Synthonix (Wake Forest, N.C., USA) and Vertellus (Indianapolis, Ind., USA), respectively. Phosphate Buffered Saline (PBS) (lx, pH=7.4) was purchased as a solution from Invitrogen (Carlsbad, Calif., USA). Hydrochloric acid (1.0N) and sodium bicarbonate were purchased from Fisher Scientific (Fair Lawn, N.J., USA). 1,2-distearoyl-sn-glycero-3-phosphoethanolamine-N-[methoxy(polyethylene glycol)-550] (ammonium salt) (DSPE-mPEG550) was purchased from Avanti Polar Lipids, Inc. SKH1-E mice were acquired from Charles River Laboratories International Inc. (Wilmington, Mass.).

Boronic Acid Synthesis. To control response, BA1 was systematically functionalized with alkyl chains of various lengths (FIG. 1). The synthesis protocol has been previously developed by Steglich and coworkers. (Neises, B.; Steglich, W. *Angewandte Chemie International Edition in English* 1978, 17, 522). Specifically, 200 mg BA1 (1.09 mmol, 1 Eq.) was mixed with 40 mg DMAP (0.33 mmol, 0.3 Eq.) and alcohol 2 (3.27 mmol, 3 Eq.) in 4 mL DMF. DCC solution in xylene (60% w/v) (1.09 mmol, 1 Eq.) (220 μL) was added dropwise to the reaction mixture at 0° C., which was then warmed to room temperature and stirred overnight. The urea precipitate was removed by centrifugation and then the supernatant was extracted with 20 mL ethyl acetate and 0.5M HCl aqueous solution. This process was repeated three times. The product was washed with saturated $NaHCO_3$ aqueous solution and then brine (saturated sodium chloride solution). The organic phase was dried over $Na_2SO_4$ and further purified by flash column chromatography. The product was characterized by $^1H$ NMR recorded on a Varian Inova 500 MHz NMR spectrometer. $^1H$ NMR data is available in the supplementary information.

Optode Composition. Macrosensors, nanofiber scaffolds, and nanoparticle-based sensors were formed from optode cocktails containing all sensing components. Macrosensors were made from the following components: 30 mg PCL, 60 μl Citroflex A6, 83.3 μmol of a boronic acid (BA) derivative (BA2b-BA2c), 2.0 mg (3.49 μmol) TDMAC, and 1.0 mg (4.16 μmol) alizarin. These materials were placed into a glass vial and then dissolved in 500 μl THF. The boronic acids incorporated into these formulations were BA1, and BA2a-c. For production of electrospun scaffolds, the general optode cocktail was made with a solution of 12% (weight/volume) of PCL in Citroflex A-6 and THF. Of this weight percentage, 10% was Citroflex A-6. Specifically, the optode formulation was: 216 mg PCL, 24.0 μL Citroflex A-6, 2.0 mg (3.49 μmol) TDMAC, 1.0 mg (4.16 μmol) alizarin, and 83.3 μmol boronic acid in 2 ml THF. Three boronic acids, 2a, 2b and 2c, were tested in electrospun scaffolds. Nanoparticle-based sensors were fabricated with an optode formulation previously described and include: 30 mg high molecular weight PVC-COOH, 60 μl DOS, 3.0 mg octylboronic acid, 4.0 mg TDMAC, and 1.0 mg alizarin. These materials were transferred into a glass vial and then dissolved in 500 μl THF.

Response of Macrosensors to Glucose. Prior to miniaturization to the nanoscale, each new BA was assessed as a glucose-sensitive macrosensor. The method for testing macrosensor responses has been described previously. (Billingsley, K.; Balaconis, M. K.; Dubach, J. M.; Zhang, N.; Lim, E.; Francis, K. P.; Clark, H. A. *Anal Chem* 2010, 82, 3707.) Briefly, macrosensors are formed by pipetting 2 μL of optode onto glass discs adhered to the bottom of an optical bottom 96-well plate. The optodes were then allowed to dry at least 15 minutes forming thin film macrosensors. A Spectramax Gemini EM micro plate fluorometer (Molecular Devices, Sunnyvale, Calif., USA) acquired fluorescence data (ex/em: 460/570 nm). After forming macrosensors, each macrosensor was hydrated in 200 μL PBS (pH=7.4) for 45 minutes. This process was repeated 4 times until the fluorescence intensity stabilized. After the macrosensors were hydrated, the PBS solution was removed from all wells and 200 μl of 0.1M glucose in PBS was pipetted into half of the wells to determine macrosensor response to glucose. The remaining wells acted as controls and contained fresh, glucose-free PBS. Changes in fluorescence response were monitored for 60 minutes at a sampling rate of 5 minutes. The fluorescence intensity of each sensor was normalized to time zero and then the mean was taken for both the experimental and control groups. The average of the experimental group was subtracted from the control group and multiplied by 100 to obtain a percent change. The error of percent change was calculated using error propagation.

Fabrication of Fibrous Scaffolds: Electrospinning was performed on a Nanospinner NE 200 (Inovenso, Istanbul, Turkey) equipped with a syringe pump. The optode solution was spun at a distance of 10 cm from the collector with a rate of 3 ml/hr and at an applied voltage of 15 kV. The fibers were spun onto either aluminum foil or silanized glass discs attached to aluminum foil for imaging and testing scaffold response.

Nanofiber Scaffold Responses to Glucose: To determine scaffold response to glucose, scaffolds spun onto glass discs were removed from the aluminum foil using a 6 mm biopsy punch (Miltex, Inc., Plainsboro, N.J., USA) and placed in a 96-well optical bottom well plate. PBS (200 μL) was added to each well and the sensors were hydrated in PBS overnight to stabilize the fluorescence intensity. All fluorescence measurements (ex/em: 460/570 nm) were acquired using a SpectraMax Gemini EM plate reader. After hydration, the PBS was replaced with 200 μL of fresh PBS (pH 7.4) as a control or 0.1M glucose in PBS (pH 7.4). The fluorescent responses were measured for 60 minutes at 5-minute intervals. Fluorescence measurements were normalized to the first time point and averaged for each experimental group. The average response of the experimental group was subtracted from the control group and then plotted over time. Error was determined using error propagation.

Fluorescence Imaging: Images of scaffolds were acquired on a Zeiss Confocal Microscope (Thornwood, N.Y.) using a 488 nm laser and 10× air objective (PlanApo, NA=0.17). The laser intensity was set to 1% (10 mW full power).

SEM Acquisition: Images of scaffolds were acquired on a Hitachi S4800 with a 5 kV accelerating voltage. Samples were not sputter coated. Fiber diameters were measured using Quartz PCI (Quartz Imaging Corp.) software. Magnification—10×, NA—0.45 in.

Fabrication of Nanoparticle-based Sensors: Nanoparticle-based sensors are fabricated as follows. Optode was dried overnight on a glass plate, and then transferred into a scintillation vial. Then 5 ml of PBS (pH=7.4) and 5 mg of DSPE-mPEG (550) in 500 μL of chloroform was added. The mixture was sonicated for 3 minutes at 40% amplitude using a Branson digital sonifier (Danbury, Conn.). The nanosensor solution was pipetted out from vial leaving residual optode.

In Vivo Studies: Animal procedures were approved by Northeastern University's Institutional Animal Care and Use Committee. To determine whether nanofiber scaffolds minimized sensor diffusion in vivo, glucose nanosensors and scaffolds were prepared as above. Scaffolds were cut into circular pieces using a 6 mm diameter biopsy punch and sterilized by soaking in 70% ethanol and then sterile PBS (pH=7.4). SKH1-E mice were anesthetized and then injected with 20 μL of either nanosensors or scaffolds along their back. To determine the injection volume, the amount of sensor material in a 6 mm diameter scaffold was estimated and then approximated to the same amount of material in the nanosensor formulation. Nanosensors were injected with 31G insulin syringes (BD Biosciences, Franklin Lakes, N.J.). Scaffolds were injected using an indwelling needle assembly. The assembly consisted of a 20 G outer needle and a 25 G inner needle with a blunted tip that acted as the plunger. 3M Vetbond™ tissue adhesive (3M Animal Care Products, St. Paul, Minn.) was then applied to the injection site. Imaging was performed on an IVIS Lumina II (Perkin Elmer) small animal imager in fluorescence mode with a 465/30 excitation filter and 580/20 emission filter. Mice were imaged every 5 minutes for 1 hour and then at 3 hours post-injection. Fluorescence measurements were analyzed by selecting a region of interest around each injection spot to obtain the total radiant efficiency of the area. The background-subtracted total radiant efficiency from each region of interest containing either scaffolds or nanosensors was measured at each time point and then normalized to the total radiant efficiency at time 0. The normalized values were then averaged across three mice for both the scaffolds and nanosensors. To account for sensor degradation over time, scaffolds and nanosensors were prepared as above and placed into a 96-well plate with a total volume of 200 μL of either PBS or PBS and nanosensors. Their total radiant efficiency was tracked using the same imaging parameters and data analysis as the in vivo studies.

Results and Discussion

Boronic Acid (BA) Selection. The clinical utility of glucose-responsive nanosensors depends on their ability to exhibit proper dynamic range and sensitivity. In the sensors presented here, the boronic acid sensing moiety governs the sensor response to glucose. The sensors respond to glucose by a competitive binding interaction between boronic acids and diols on either alizarin or glucose. In the absence of glucose, the boronic acid binds to the diol on alizarin, statically quenching its fluorescence. As local glucose concentrations increase, those molecules displace the alizarin, allowing it to fluoresce.

We derivatized phenylboronic acids containing fluoro- and carboxyl-groups that withdraw electrons in order to improve sensor response compared to previous designs by improving boronic acid binding to diols at physiologic pH. In addition to acting as an electron-withdrawing group, carboxyls provide a site for the alkyl chain additions performed herein and other chemical modifications.

Figure 2:
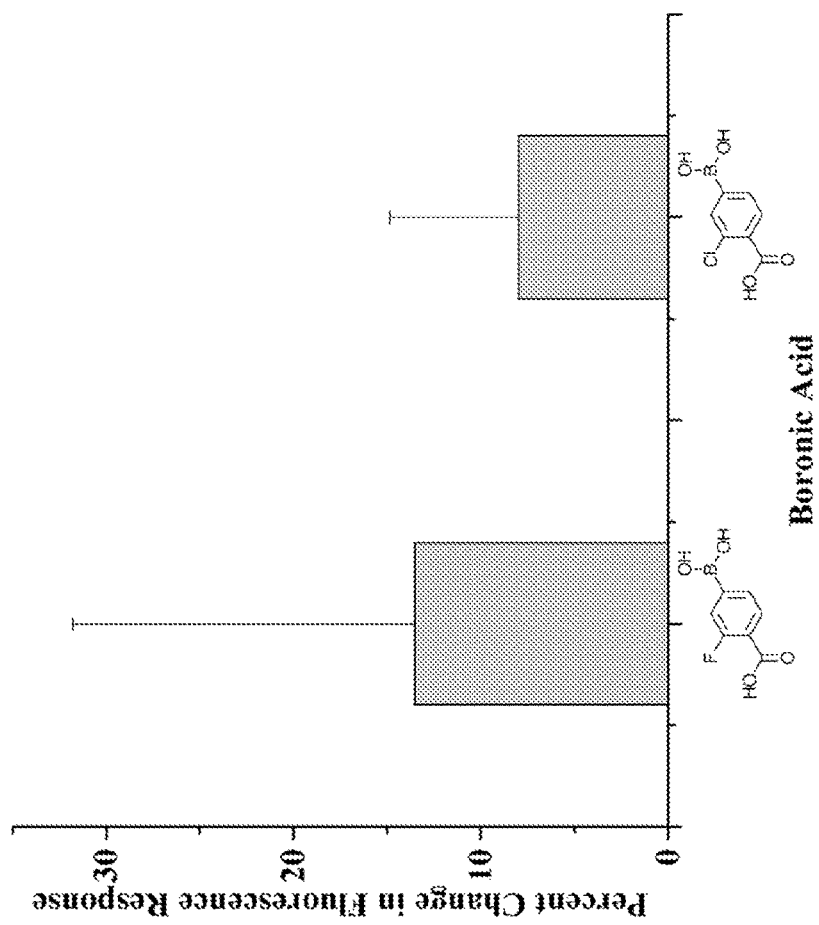
FIG. 2 illustrates the response of glucose-sensitive macrosensors containing boronic acids with different electron withdrawing groups. The macrosensors contained either Boronic Acid 1a ($n_{control}=7$, $n_{glucose}=8$) or Boronic Acid 1b ($n_{control}=8$, $n_{glucose}=8$). Macrosensors were exposed to either PBS as a control or 100 mM glucose in PBS for 60 minutes. The percent change in fluorescence response was calculated as the average normalized difference between the control and glucose groups. Error bars were calculated using error propagation.

The initial screen for glucose-responsiveness showed that macrosensors with 4-carboxy-3-fluorophenyl boronic acid (BA1) increased fluorescence 13% from baseline in response to 100 mM glucose (FIG. 2). This compound's reactivity derives from having both fluoro- and carboxyl groups withdrawing electrons from the boronic acid group, however this increases the compound's polarity. Consequently, BA1 readily leached from the hydrophobic sensor platform over time (FIG. 3), which leads to signal degradation and loss of sensitivity to glucose. We then produced a new set of boronic acid molecules with varying polarities by systematically converting the carboxyl group into esters with various alkyl chain lengths to find responsive and stable sensors.

Figure 3:
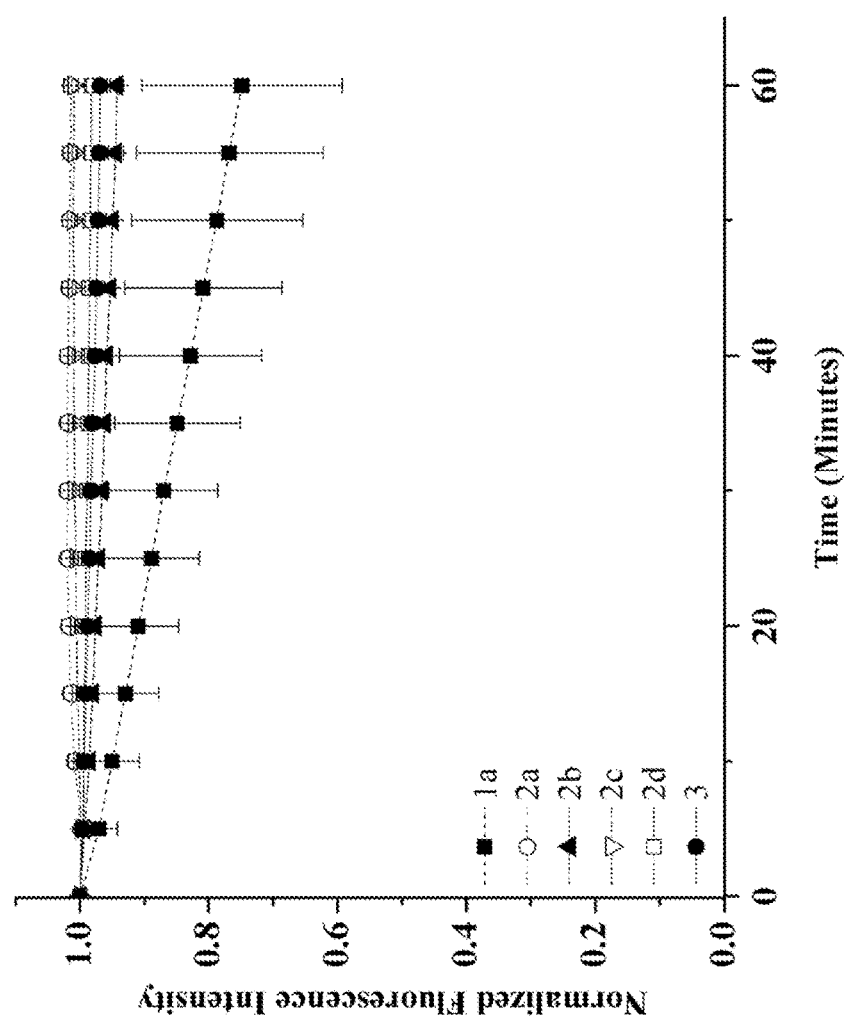
FIG. 3 shows the fluorescence decay of macrosensors with different boronic acids. The macrosensors contained Boronic Acids 1a (n=7), 2a (n=7), 2b (n=7), 2c (n=8), 2d (n=8), or 3 (n=8) and were exposed to PBS for 60 minutes. Fluorescence intensities were normalized to time 0 and error bars represent standard deviations.
Figure 4:
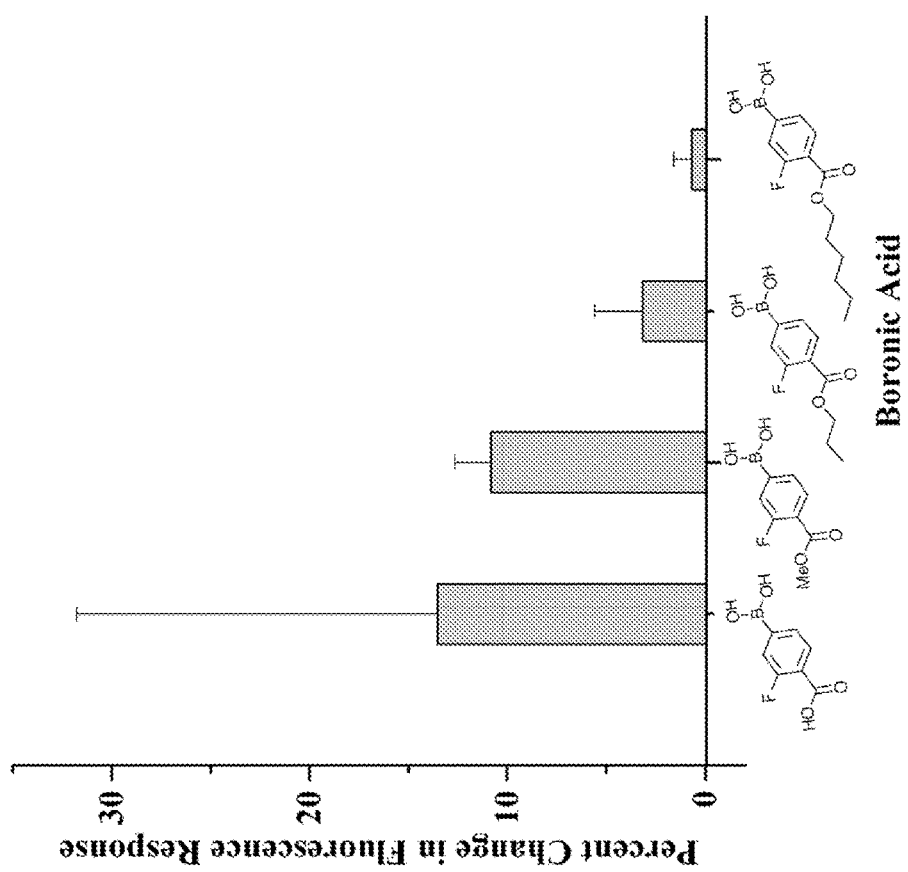
FIG. 4 is a graph showing the response of glucose-sensitive macrosensors containing functionalized boronic acids with increasing length of alkyl chains. The macrosensors contain Boronic Acids 1a ($n_{control}=7$, $n_{glucose}=8$), 2a ($n_{control}=7$, $n_{glucose}=7$), 2b ($n_{control}=7$, $n_{glucose}=7$), or 2c ($n_{control}=8$, $n_{glucose}=8$). Macrosensors were exposed to either PBS as a control or 100 mM glucose in PBS for 60 minutes. The percent change in fluorescence response was calculated as the average normalized difference between the control and glucose groups. Error bars were calculated using error propagation
Figures 5A, 5B, 5C:
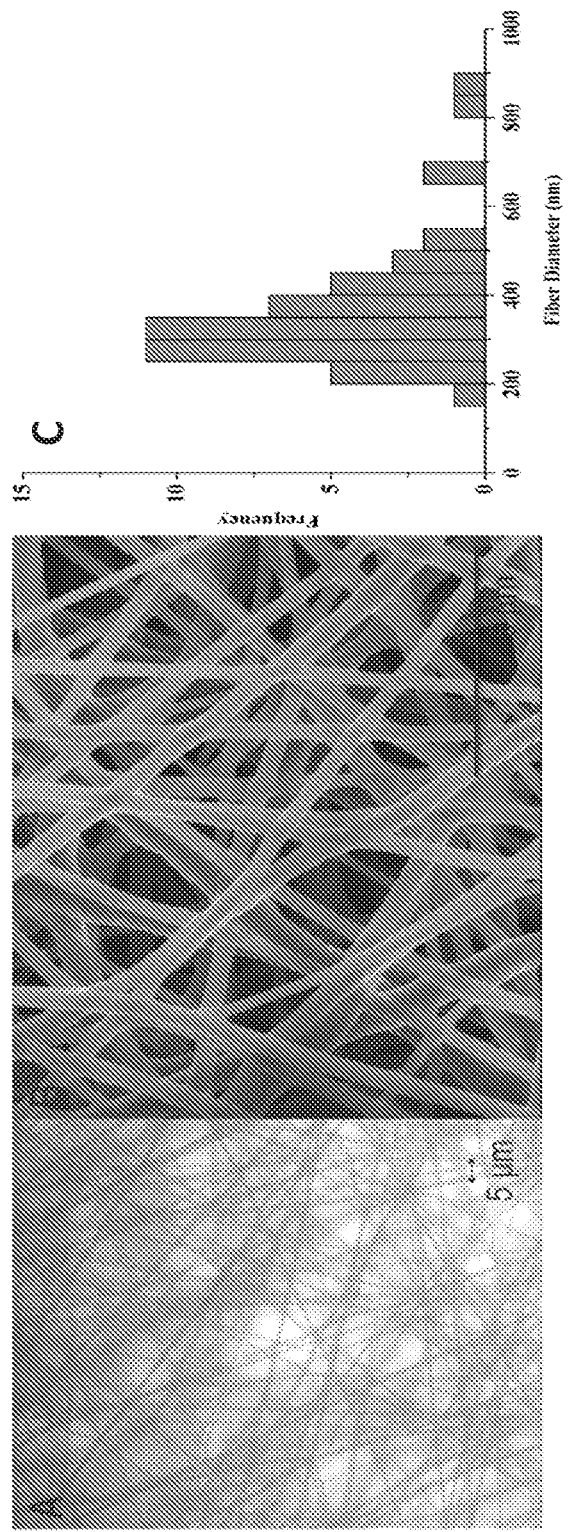
FIG. 5A is a confocal image.
FIG. 5B is an SEM image.
FIG. 5C is a plot showing size distribution of glucose-sensitive nanofibers. The average fiber diameter was 374±142 nm (n=49). The width of histogram columns represent 50 nm.

Adding a methyl ester to BA1 produced BA2a, which leached out of the macrosensors significantly less than BA1, and longer alkyl chains (BA2b &BA2c) produced no significant reduction in leaching compared to the methyl ester (FIG. 3). Increasing the alkyl length decreased the resulting boronic acid's reactivity; the magnitude of macrosensor responses to glucose when formulated with BA2a, BA2b, and BA2c were all less than compared to macrosensors made with BA1. Macrosensors with BA2a were still relatively sensitive at physiological pH, exhibiting a 10% increase in fluorescence in response to 100 mM glucose. By contrast, macrosensors made with BA2b and BA2c only increased by 3% and less than 1%, respectively (FIG. 4).

The nanosensors' competitive binding mechanism depends on the boronic acid diffusing within the hydrophobic matrix and interacting with glucose molecules at the sensor-environment interface. The result that longer alkyl chains reduced the magnitude of sensor responses suggests that long alkyl chains inhibited boronic acid diffusion within the polymer matrix. While leaching is much less problematic for those derivatives such as BA2c, the increased hydrophobicity may impart too high of an affinity to polymer matrix, causing sluggish diffusion and small sensor responses.

Glucose-sensitive nanosensors containing octylboronic acid, a hydrophobic aliphatic derivative, as the sensing moiety, although stable in the hydrophobic nanosensor core, were not sufficiently sensitive to glucose. Applicants have determined that 4-carboxyl-3-fluoroboronic acid and its derivatives are more sensitive to glucose due to their fluoro- and carboxyl groups. With the results showing that BA2a leaches significantly less than BA1 and is must more responsive to glucose than BA2b and BA2c, BA2a was considered to be particularly useful for nano-scale sensor fabrication.

Glucose-Sensitive Nanofibers. In addition to improvements in nanosensor sensitivity, nanosensor systems need new design strategies for increasing residency time at the implantation site, ideally with minimally-invasive delivery methods. Glucose nanosensors with BA2a were electrospun to produce nanosensors with nanofiber architectures, requiring a plasticizer content of 10%. For comparison, spherical nanosensors were also made using the fabrication method described in the Materials and Methods section. Electrospinning optodes with 70-90 kDa PCL successfully produced continuous polymer nanofibers, as confirmed with SEM images for high resolution fiber measurements and with confocal images to show homogenous fluorescence from the alizarin within the fibers (FIG. 4). Measurements from the SEM images indicate that fiber diameters were 374±142 nm and were continuous without beading or wetting. Optode-based sensors are typically highly plasticized to aid the mobility of sensor components and analytes within the sensor. Nanofibers that were electrospun with PCL and 30% or 60% plasticizer increased the glucose-sensitivity by 6%. However, even the 30% plasticized scaffolds showed signs of electrospinning instability with discontinuous fibers and areas of pools of plasticizer (data not shown). Therefore, in order to maintain the nanofibrous structure, 10% plasticizer content was used at the trade-off of sensor response.

Figure 6B:
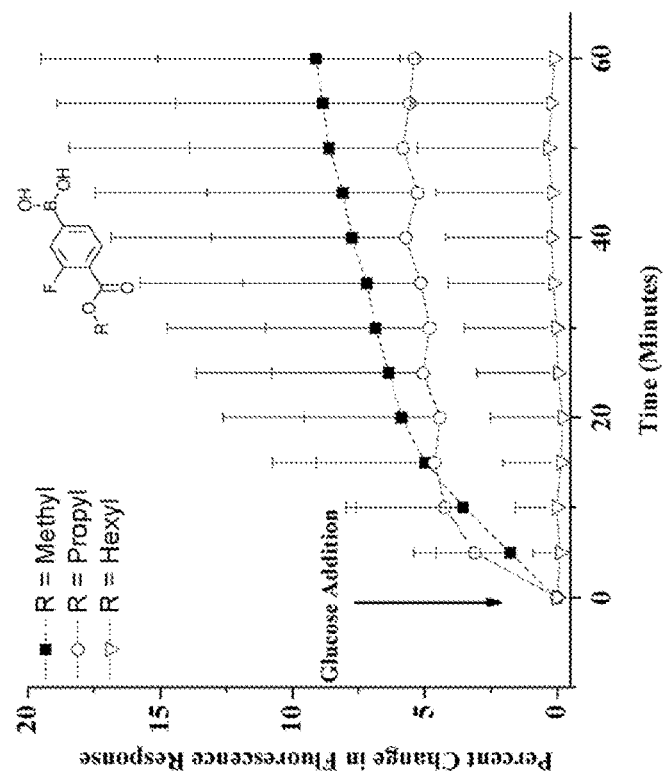
FIG. 6 presents graphs showing the response of glucose-sensitive nanofibers containing different functionalized boronic acids. Glucose-sensitive nanofibers contained fluorinated boronic acid derivatives with methyl ($n_{control}=6$, $n_{glucose}=8$), propyl ($n_{control}=5$, $n_{glucose}=7$), and hexyl ($n_{control}=7$, $n_{glucose}=8$) length alkyl chains. Increasing alkyl chain lengths on fluorinated boronic acid derivatives effected the response of glucose-sensitive nanofibers. Nanofibers were exposed to either PBS as a control or 100 mM glucose in PBS for 60 minutes. The percent change in fluorescence response was calculated as the average normalized difference between the control and glucose groups. Error bars were calculated using error propagation.
Figure 6A:
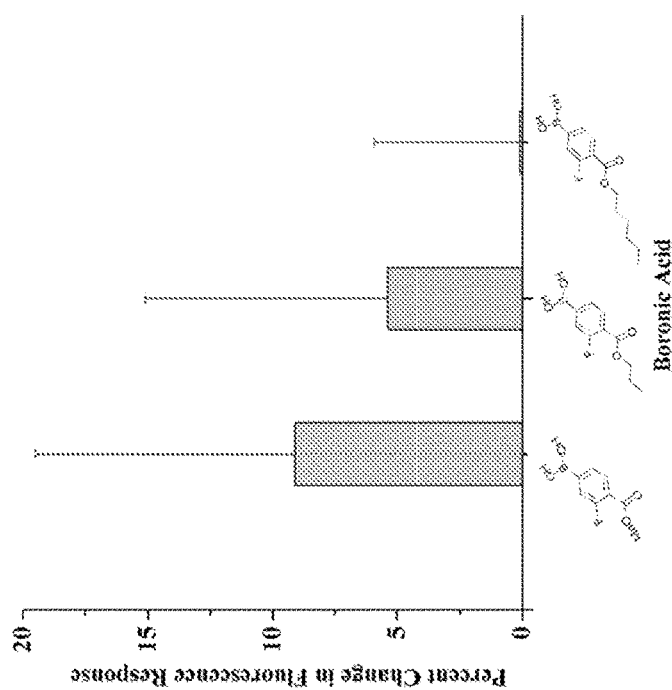

Glucose-sensitive nanofibers with Boronic Acids 2a-2c all responded slightly less than their macrosensor counterparts. Similar to their macrosensor counterparts, boronic acids with longer alkyl chains decreased the sensitivity to glucose. To test the electrospun nanosensor response times, fluorescence intensity was monitored over one hour after placing scaffolds in 100 mM glucose in PBS. Sensors containing BA2b reached 95% of their maximum response within 12 minutes, but sensors containing BA2a did not level off within an hour (FIG. 6). The slow response times are likely due to the low plasticizer content as well as the static flow conditions for the experimental configuration. Low plasticizer content would restrict components from diffusing to the sensor-environment interface. An experiment conducted in a flow cell would have enhanced the rate of solution diffusion throughout the porous scaffold and decreased the response time. Despite these slow response times, it is important to note that physiologic glucose levels change over the course of tens of minutes, meaning that the BA2b formulation in nanofiber form responds sufficiently fast to capture these changes. Higher molecular weight PCL or other polymers can support higher plasticizer percentages; for example, electrospun nanofibers fabricated with ethyl cellulose were able to support up to 40% plasticizer. Such strategies offer additional ways to improve the sensitivity and response times of future nanosensor designs.

Figure 7:
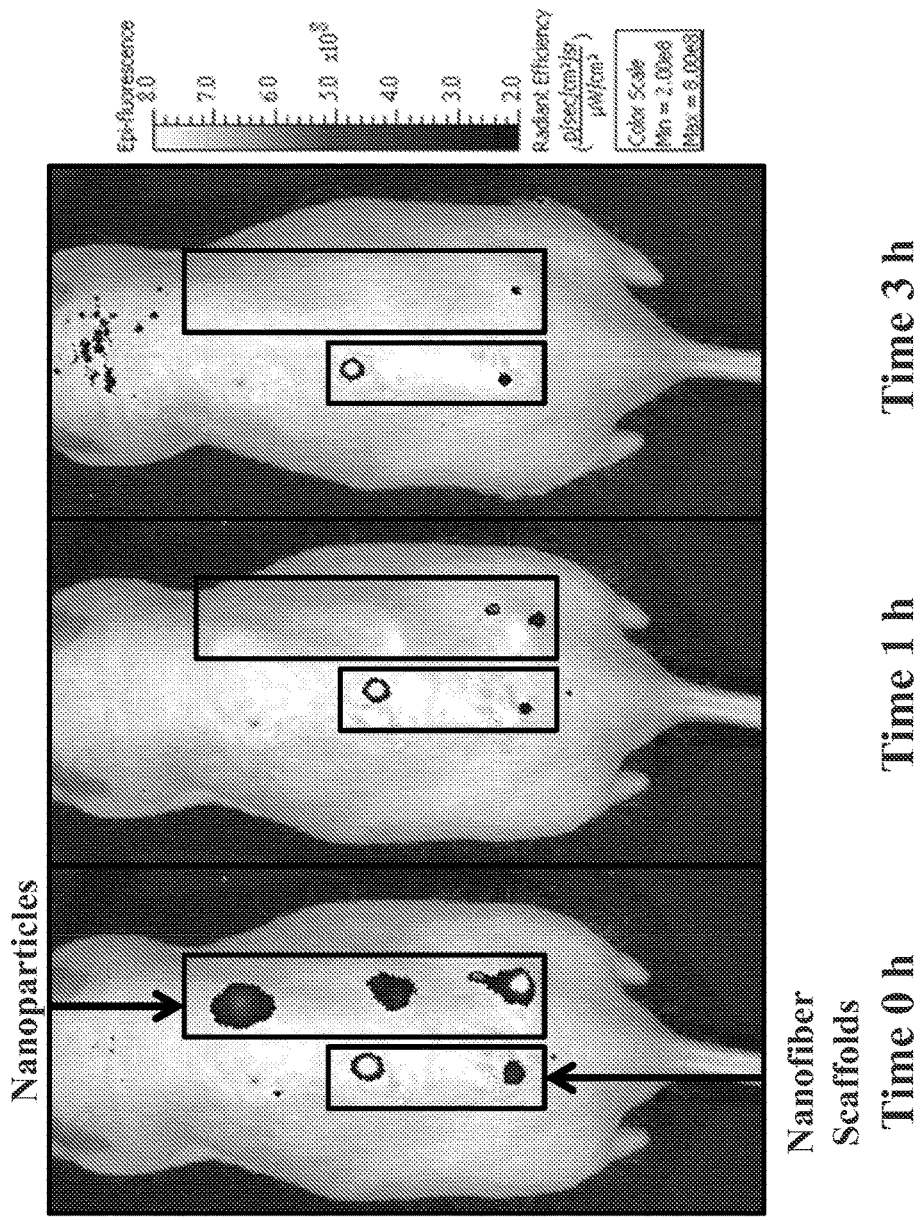
FIG. 7 provides images showing in vivo comparison of glucose-sensitive nanoparticles and nanofiber scaffolds in mice. Mice were injected with glucose-sensitive nanoparticles and nanofiber scaffolds along the back and then imaged with a fluorescent small animal imager for one hour and then at 3 hours post-injection. Shown here are the fluorescent images from one mouse over this time frame.

In Vivo Lifetime Studies. In previous in vivo studies, nanoparticle-based sensors diffused away from the implantation site within one hour. To show that nanofiber nanosensors improve residency times at the implantation site, either spherical nanosensors or nanofiber nanosensors were implanted subdermally (FIG. 7) and their signal loss was directly compared to their in vitro signal loss. Similar to previous experiments, the spherical nanosensors lost radiant efficiency at the injection site significantly greater than the signal loss observed in vitro. In vitro signal loss is attributed to boronic acid leaching from the hydrophobic core, and the difference between in vivo and in vitro signal loss is attributed to nanosensor diffusion away from the implantation site. By contrast, nanofiber scaffolds exhibited very closely matched signal loss between the in vivo and in vitro experiments after one hour, and they were nearly equal after three hours (FIG. 8). The spherical nanosensors experienced a ~30% difference in total radiant efficiency loss when compared to the in vitro control, whereas the decay constants for nanofiber scaffolds differed only by 6%.

Several factors accelerated the signal loss for spherical nanosensors in vivo compared to in vitro, most notably sensor diffusion, cellular uptake, and the potential for facilitated transport of components (either alizarin or boronic acid) out of the nanosensors due to amphiphilic serum components in the in vivo environment. Since the in vivo lifetime of the nanofiber scaffold compared to the nanoparticles was increased almost to the levels observed with the nanofibers in vitro, one can conclude that the new sensor geometry maintained sensor residency at the injection site and would allow for longer monitoring times.

CONCLUSION

The present application discloses optode-based glucose nanosensors that are more sensitive to glucose and more stable at the site of in vivo implantation. The initial macrosensor screen showed that electron-withdrawing groups on BA1 and its derivatives facilitated a response to glucose under physiological conditions, which is a major improvement over previous hydrophobic boronic acid derivatives. Using the most responsive hydrophobic boronic acid derivative, BA2a, nanosensors were electrospun into nanofibers and the nanofiber format was significantly more stable in vivo than spherical nanosensors.

Example 2: Sodium-Sensitive Electrospun Scaffolds

Example 2 of this platform is the demonstration of sodium-sensitive scaffolds. The mechanism is a three component system based on traditional optode sensor components: a sodium-specific ionophore, fluorescent pH-sensitive dye, and a negatively charged additive. When sodium is present, the ionophore selectively extracts sodium ions into the sensor. To maintain charge neutrality within the sensor, the pH-sensitive dye deprotonates resulting in a change in sensor fluorescence. The intensities at the 570 nm and 680 nm were ratioed and alpha was calculated as:

$$\alpha = \frac{(\text{Ratio}_{Max} - \text{Ratio}_{[Na+]})}{(\text{Ratio}_{Max} - \text{Ratio}_{Min})}$$

where RatioMax is the ratio in the fully deprotonated state, RatioMin is the ratio in the fully protonated state, and Ratio[NA+] is the ratio at a specific sodium concentration. The response of the sensors can be tailored by changing the ratio of sensing components.

Figure 10:
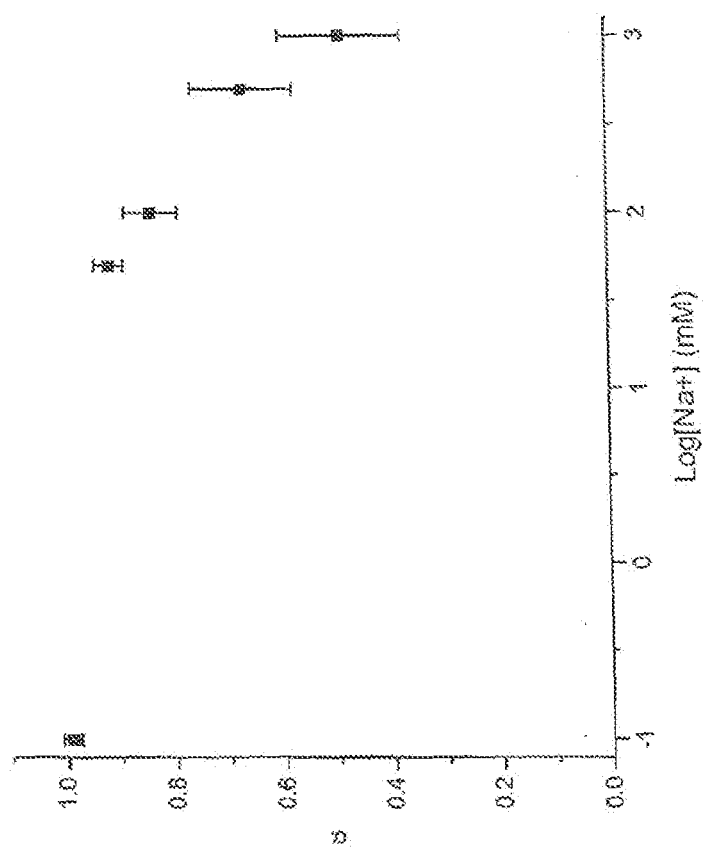
FIG. 10 shows the response of sodium-sensitive scaffolds to sodium. Calibration curve of sodium-sensitive scaffold response to increasing concentrations of sodium. Error bars represent standard deviations (n=7).

PCL-nanofibers for use in measuring sodium contain a hydrophobic core that isolates the interior components from the surrounding aqueous environment. The fibers are made of a plasticized polymer and the core contains the ionophore, which extracts the ion into the core, resulting in deprotonation of chromoionophore; the presence of the negatively charged additive helps to maintain charge neutrality during the proton exchange. Nanofiber sensors were evaluated in human serum samples and mice for detection of sodium. As shown in FIG. 9A, nanofibers can be injected as whole scaffolds using an indwelling needle assembly. Alternatively, as shown in FIG. 9B, nanofibers can also be sonicated to form "whiskers" that can be injected like nanosensors. In serum samples, the nanofibers detected spiked sodium levels in serum as reliably as a commercially-available diagnostic. See FIG. 10. In vivo, the nanofibers remained at the site of injection and thus extended monitoring times of the sensors.

In an effort to improve response of the nanofibers to sodium, the composition may be modified by including an additive, such as 2 mg of NaTFPB. The nanofiber scaffolds are reversibly responsive to exposure to 1M NaCl and washing with HEPES buffer. Results also show that the nanofiber scaffolds are equally responsive to sodium in the presence of background potassium, indicating that the scaffolds are sensitive to sodium, not simply ionic strength. Moreover, the nanofiber scaffolds function for at least 7 days.

Example 3: Calcium-Sensitive Electrospun Scaffolds

Figure 11:
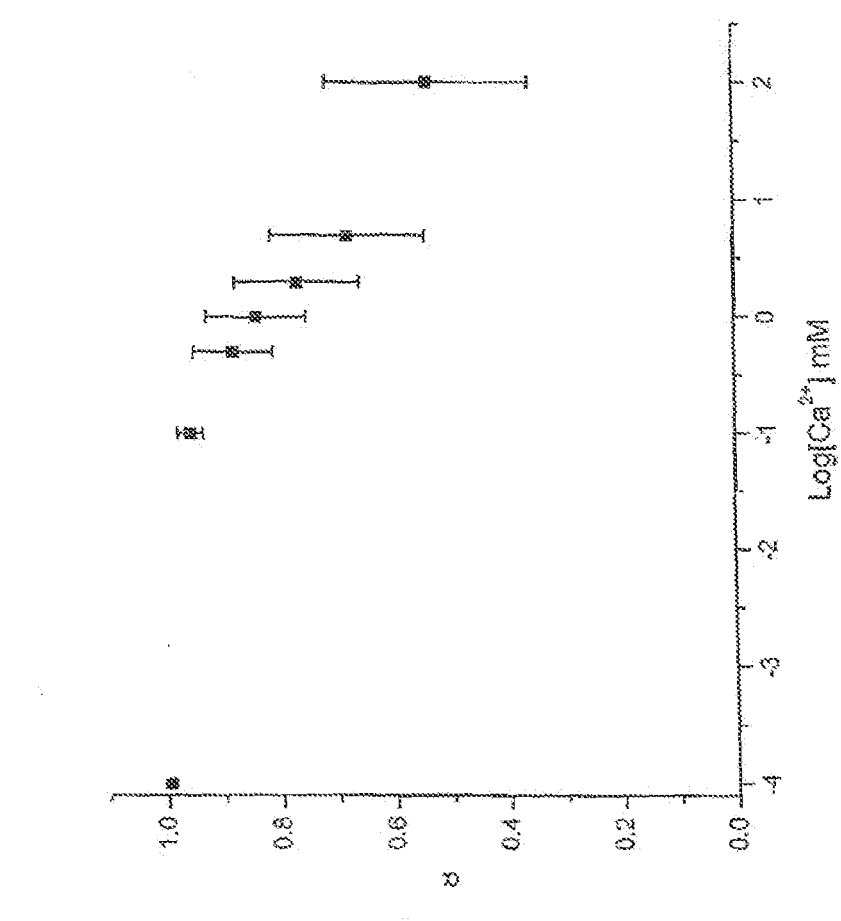
FIG. 11 shows the response of calcium-sensitive scaffolds to calcium. Calibration curve of calcium-sensitive scaffold response to increasing concentrations of calcium. Error bars represent standard deviations (n=6).

Example 3 of this platform is the demonstration of calcium-sensitive scaffolds. The mechanism is similar to sodium-sensitive scaffolds except that the sodium-specific ionophore is substituted for a calcium-specific ionophore. FIG. 11 shows the calibrated response of calcium-sensitive fibers to increasing concentrations of calcium. Alpha is calculated the same as in Example 2.

Test results also show that different amounts of calcium ionophore II (CaII) yield different responses of the nanofibers to calcium and different amounts of additive (KTFPB) yield different responses of the nanofibers to calcium.

Example 4: Injectable Fibrous Sensors

Injectable fibrous sensors are desirable for easy implantation in vivo. Fibrous sensors were electrospun into a sheet and then placed into a mixture of 1,2-distearoyl-sn-glycero-3-phosphoethanolamine-N-[methoxy(polyethylene glycol)-550] (ammonium salt) (PEG-lipid) and 250 mM of sodium hydroxide (NaOH). NaOH induces hydrolytic degradation of polycaprolactone. After 17 hours, the scaffold in the PEG-lipid/NaOH solution was fragmented using ultrasonication. The fibers were then centrifuged and resuspended in a buffer solution to generate individual fibers (nanowhiskers). Other methods for forming injectable fibrous sensors will include but are not limited to using various acids or bases at different concentrations for inducing hydrolytic degradation of scaffolds and enzymes for enzymatic degradation of scaffolds.

Example 5: Nanofiber Scaffold Response to Chloride

Figure 12A:
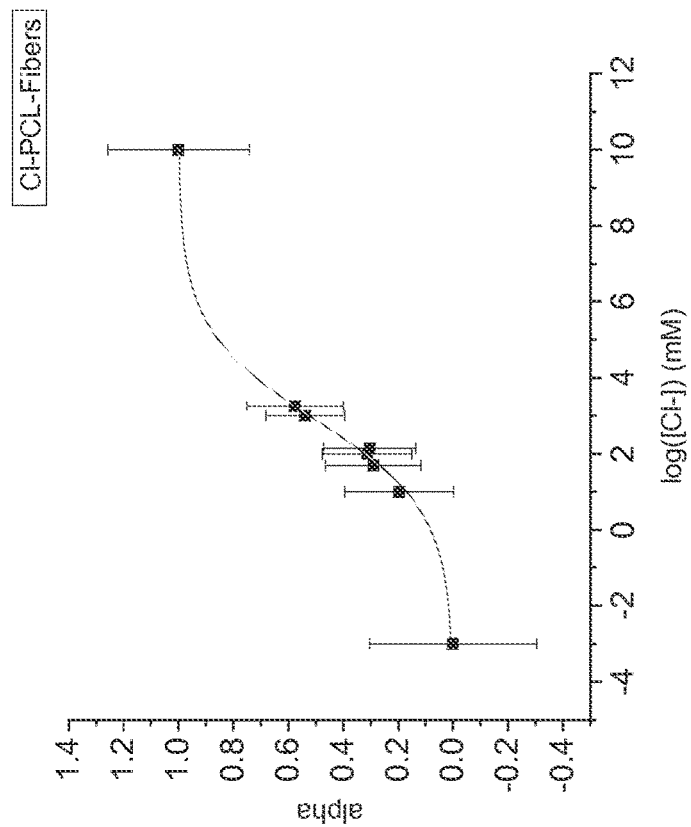
FIG. 12A shows PCL-based nanofibers response to chloride.
Figure 12B:
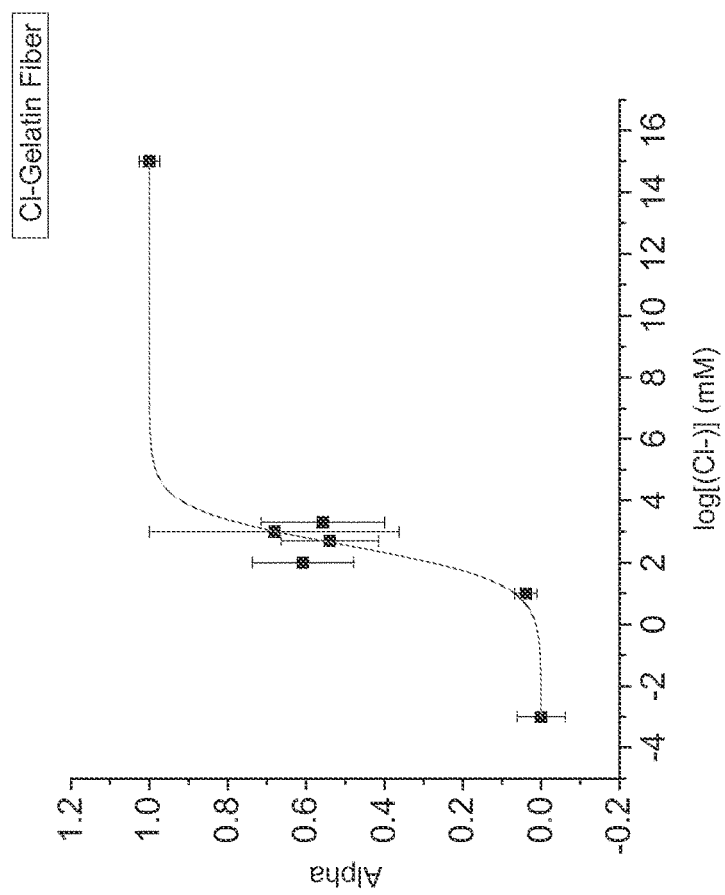
FIG. 12 provides graphs showing nanofiber scaffold response to chloride.

FIG. 12A shows PCL-based nanofibers response to chloride and FIG. 12B shows nanosensors electrospun into gelatin fibers response to chloride.

Example 6: Detection of Stimulus-Induced Serotonin Released from Co-Cultured Platelet Progenitor Cells Using Phosphorescent Nanofibers Serotonin is implicated in the control and function of a host of bodily functions, acting as a neurotransmitter, hormone, and cardiovascular growth factor. Detecting the release of serotonin in whole blood can be an important diagnostic tool in assessing conditions such as depression, schizophrenia, carcinoid syndrome, and cardiovascular disease. Current techniques for the detection of serotonin levels in whole blood can be time consuming and destructive. A nondestructive and fast method for the detection of stimulus-induced serotonin released from co-cultured platelet progenitor cells using phosphorescent nanofibers is disclosed herein.

These nanofibers have a hydrophobic core, which contains an oxygen-sensitive dye and a reference dye, as well as a collagen exterior conjugated to monoamine oxidase (MAO). MAO converts secreted serotonin to a metabolite by consuming environmental oxygen. This conversion leads to localized deoxygenated areas which cause the interior oxygen sensitive dye to phosphoresce, indicating the presence of serotonin. This response has been tuned to an optimal sensitivity, response time, specificity over competing analytes, and sensor lifetime, thus yielding a reversible sensor that quantitatively detects serotonin in vitro and operates in real time. A quantitative increase in phosphorescence in response to serotonin released by platelet progenitor cells and late stage platelets was determined. In response to buffer treatment phosphorescence levels decreased, demonstrating the reversibility of these nanofibers. Oxygen-sensitive nanosensors electrospun into a collagen matrix are shown to increase the response time of serotonin-sensing nanofibers. These nanofibers have an application as a novel tool for the continuous monitoring of analytes in cellular environments.

Figure 13:
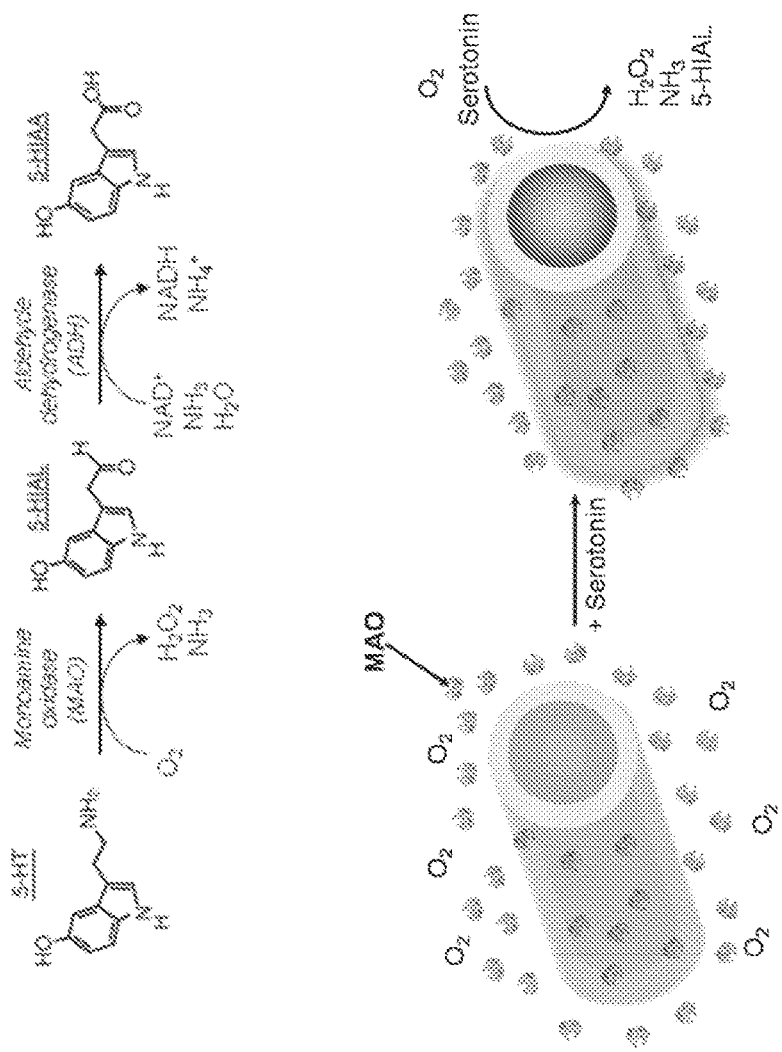
FIG. 13 shows a mechanism of PCL-based serotonin-sensing nanofibers.

As shown in FIG. 13, serotonin (5-HT) is converted by monoamine oxidase (MAO) and aldehyde dehydrogenase (ADH), consuming oxygen ($O_2$). Scaffolds were coaxially electrospun to form a plasticized polymer core and an aqueous shell containing collagen, which was covalently linked to MAO. In the absence of serotonin, solution-exposed scaffolds emit a low phosphorescent signal, which is consistent with oxygen-induced quenching. Upon addition of serotonin, MAO consumes oxygen at different rates, which results in phosphorescence emission from the scaffolds. The fibers also contain a reference dye, Rhodamine C-18, used for quantitative imaging.

FIG. 14 illustrates the phosphorescence emission characteristics of oxygen-sensitive dye. PtTFPP (Pt(II) meso-tetra (pentafluorophenyl)porphine) was used as the oxygen-sensitive dye in the nanofibers. In general, the platinum(II) complexes of TFPP possess particularly high photostability and a reasonably good phosphorescence quantum yield, compared to other oxygen-sensitive dyes. PtTFPP has an excitation peak of 395 nm and an emission peak at 650 nm.

As shown in FIG. 15, coaxial electrospinning of nanofibers allows design of compatibility and functionality. For coaxially-spun fibers, the core solution syringe was attached to the inner bore of a concentric spinning headpiece and the shell (sheath) solution syringe was attached to the outer bore. A voltage of 15 kV was applied to induce fiber formation onto 5 mm glass cover slips attached to an aluminum foil-covered collector plate or 25 mm glass cover slips attached to a rotating mandrel set at a speed of 2 rotations/second (for aligned fibers). The polymer core of the nanofiber contains the sensing components and the collagen shell can be used for cell attachment and surface chemistry.

Figure 16:
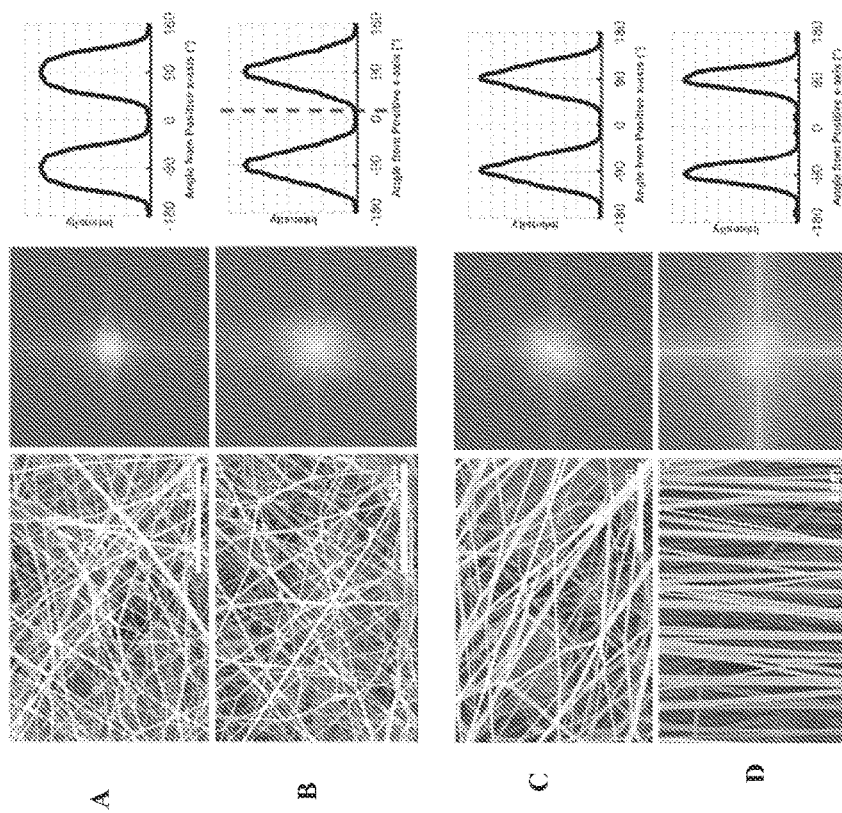
FIG. 16 shows PCL-based serotonin-sensing fibers morphology with varied spinning distances. (16A) 5 cm, (16B) 8 cm, (16C) 10 cm, (16D) 15 cm.

FIG. 16 shows PCL-based serotonin-sensing fibers morphology with varied spinning distances. (16A) 5 cm, (16B) 8 cm, (16C) 10 cm, (16D) 15 cm. The FFT spectra of the scanning electron microscopy images are shown, as well as intensity traces of the FFT spectra.

Coaxial electrospinning was evaluated using different polymer core or sheath components. PCL with either collagen or fibrinogen incorporated into a sheath do not change the emission properties of the nanofibers. Incorporation of a shell changes the average diameter and range of diameters acquired through electrospinning (n=20).

Coaxially electrospun serotonin-sensitive scaffolds prepared in accordance with the present disclosure had an average fiber diameter of 682±193 nm (n=50). FT-IR spectra comparing PCL nanofibers to PCL core nanofibers with collagen shell confirmed the presence of a collagen shell on the nanofibers.

Figure 17A:
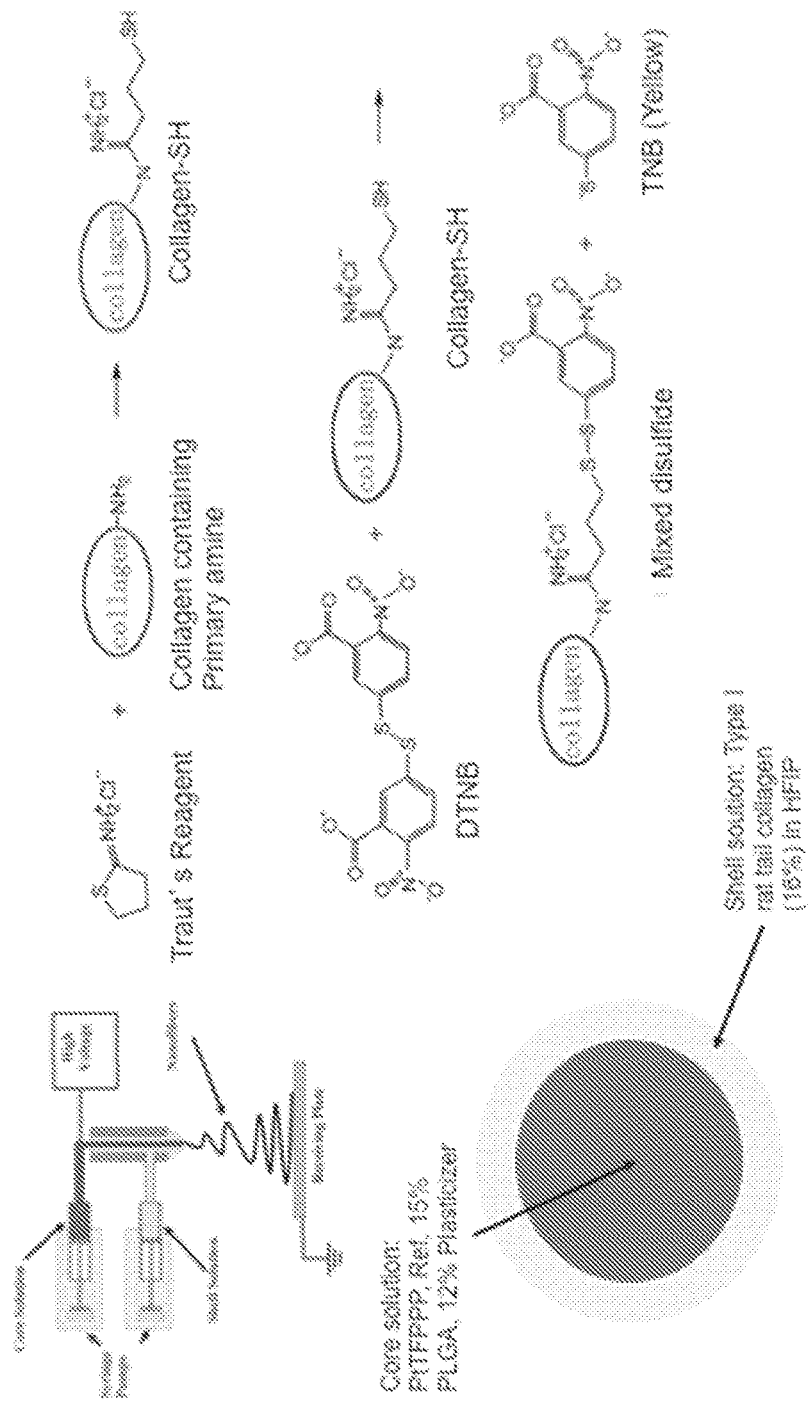
FIG. 17A illustrates a process for modifying nanofibers by Traut's reagent to make sulfhydryl-modified collagen on the core of the fibers. DTNB can be used to confirm the surface modification of the collagen. By making a calibration curve from 3-mercaptoethanol (contains one primary amine) and Ellman's reagent (FIG. 17B), one can estimate the amount of modified sulfhydryl groups incorporated according to the TNB product produced (FIG. 17C).
Figures 17B, 17C:
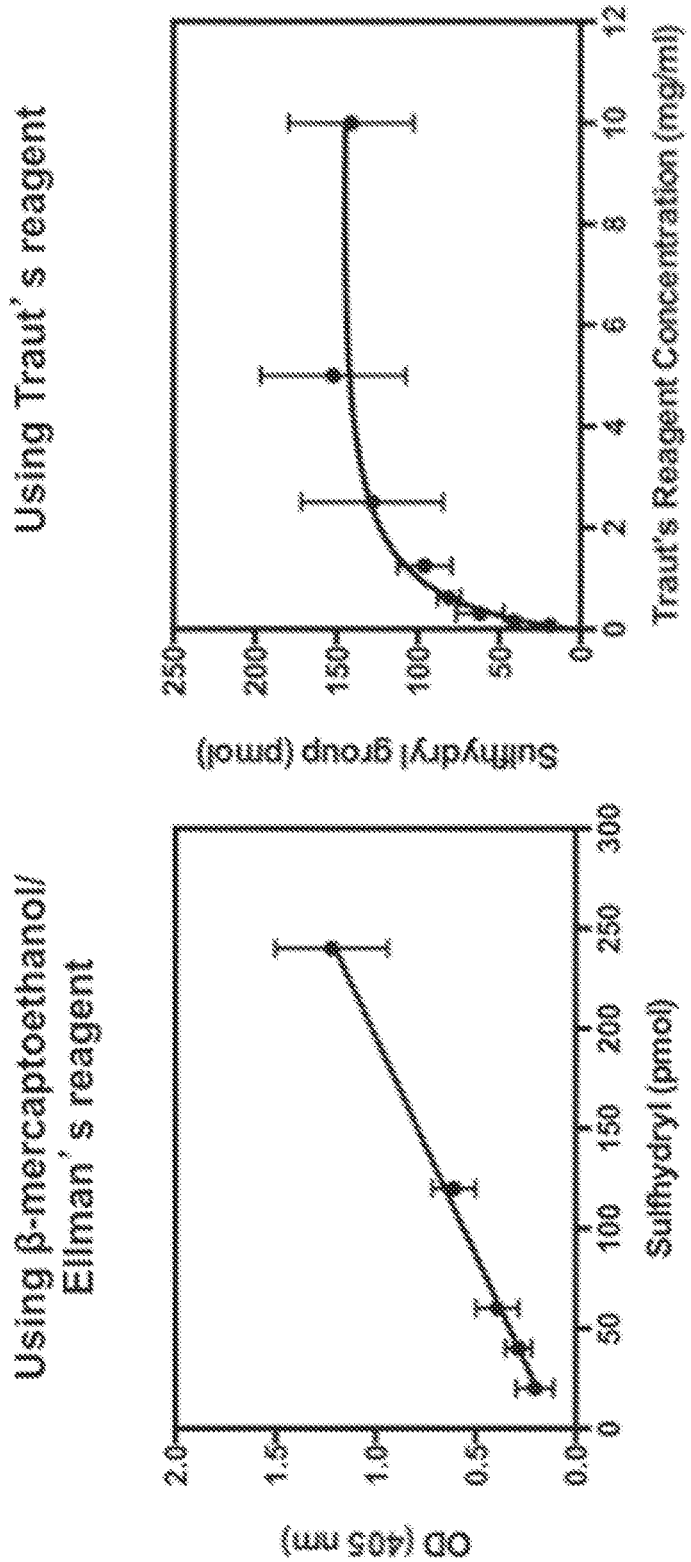
FIG. 17 illustrates the first steps for surface tethering of enzyme to nanofibers.

FIG. 17 illustrates the first steps for surface tethering of enzyme to nanofibers. FIG. 17A illustrates a process for modifying nanofibers by Traut's reagent to make sulfhydryl-modified collagen on the core of the fibers. DTNB can be used to confirm the surface modification of the collagen. By making a calibration curve from 3-mercaptoethanol (contains one primary amine) and Ellman's reagent (FIG. 17B), one can estimate the amount of modified sulfhydryl groups incorporated according to the TNB product produced (FIG. 17C).

Figure 18:
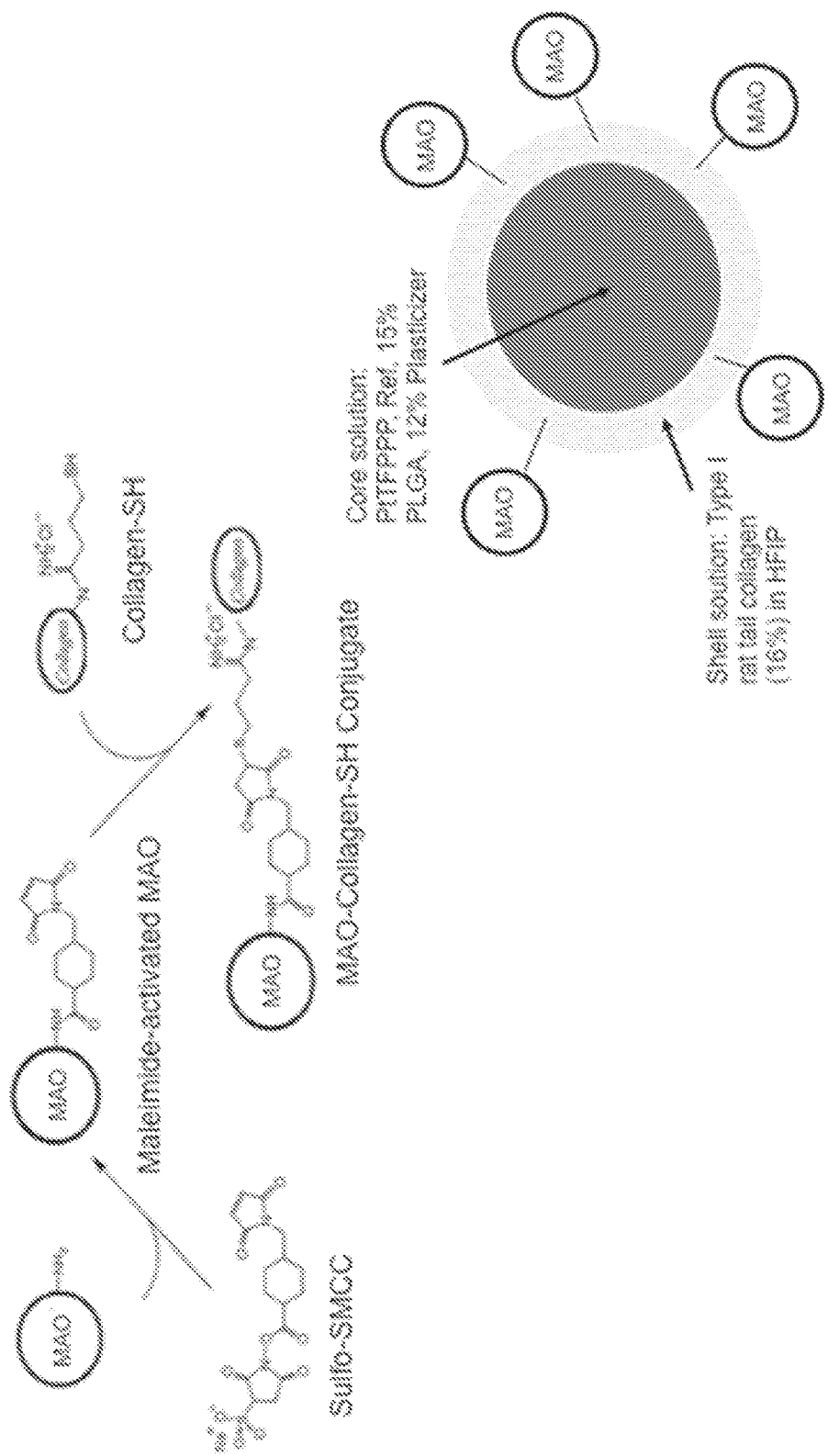
FIG. 18 describes one approach to attach enzyme to sulfhydryl-modified nanofibers.

FIG. 18 describes one approach to attach enzyme to sulfhydryl-modified nanofibers. Sulfo-SMCC was added to the monoamine oxidase A and reacted at RT overnight with the sulfhydryl-modified nanofibers to make enzyme conjugated nanofibers.

Figure 19:
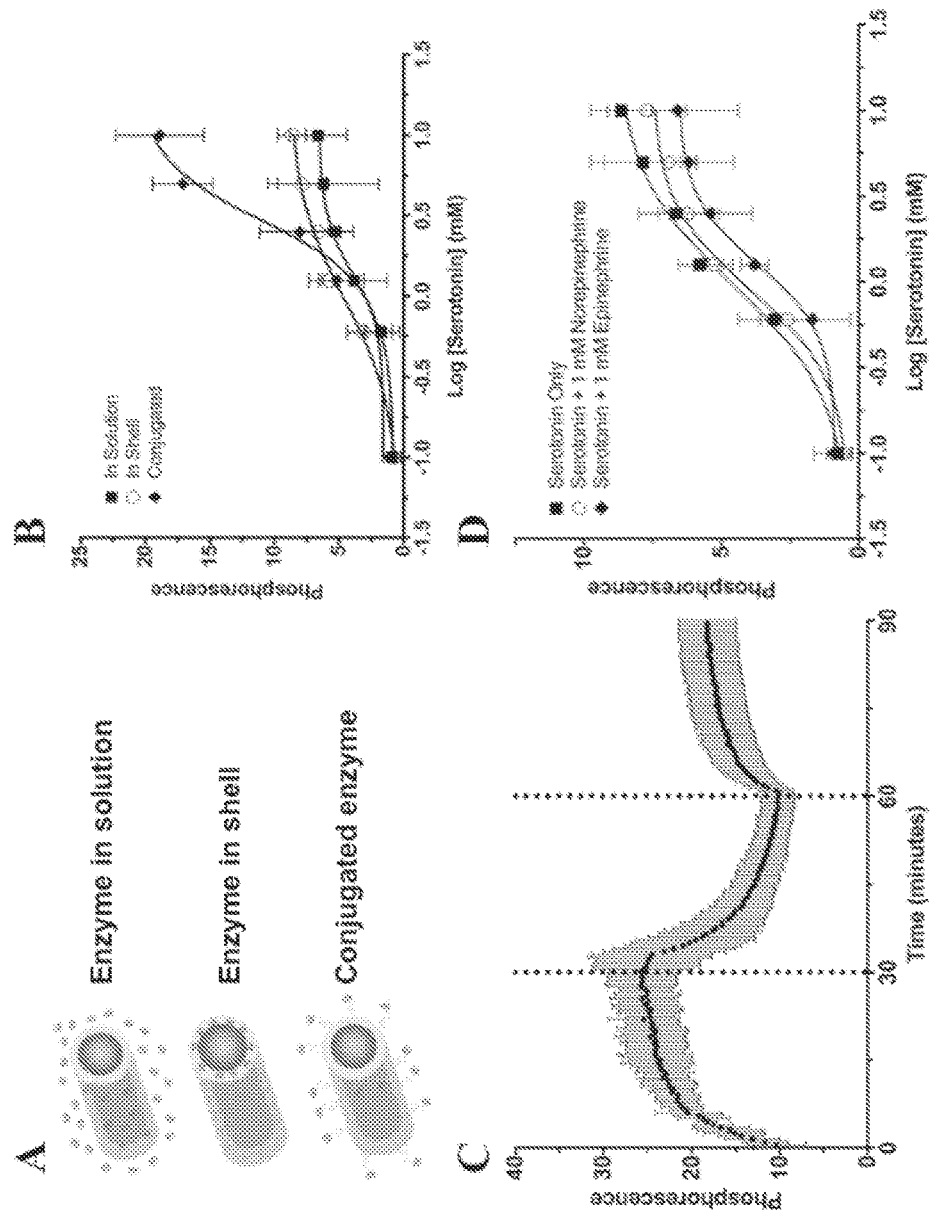
FIG. 19A is a schematic of various nanofiber designs showing enzyme in solution, enzyme in shell and conjugated enzyme.
FIG. 19B is a graph showing scaffold response.
FIG. 19C shows scaffold reversibility.
FIG. 19D illustrates scaffold selectivity.

FIG. 19A is a schematic of various nanofiber designs showing enzyme in solution, enzyme in shell and conjugated enzyme. FIG. 19B is a graph showing scaffold response, FIG. 19C shows scaffold reversibility, and FIG. 19D illustrates scaffold selectivity.

Figure 20:
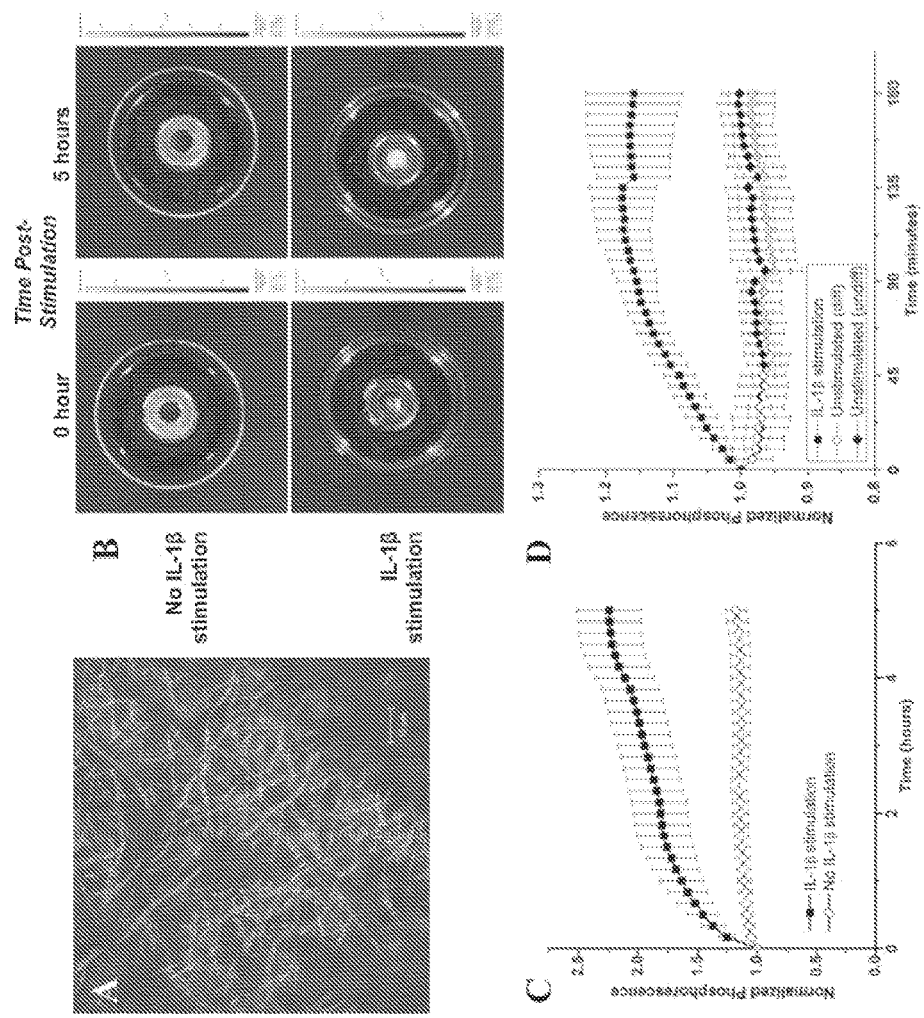
FIG. 20 shows nanofiber scaffold response to cellular serotonin.

FIG. 20 shows nanofiber scaffold response to cellular serotonin. FIG. 20A is a confocal image of scaffolds with cells grown on them (overlay of experimental and reference dyes), FIG. 20B presents fluorescent reader images of scaffolds, FIG. 20C shows the response with Meg01 cells, and FIG. 20D shows the response with T33 cells.

Figures 21A, 21B:
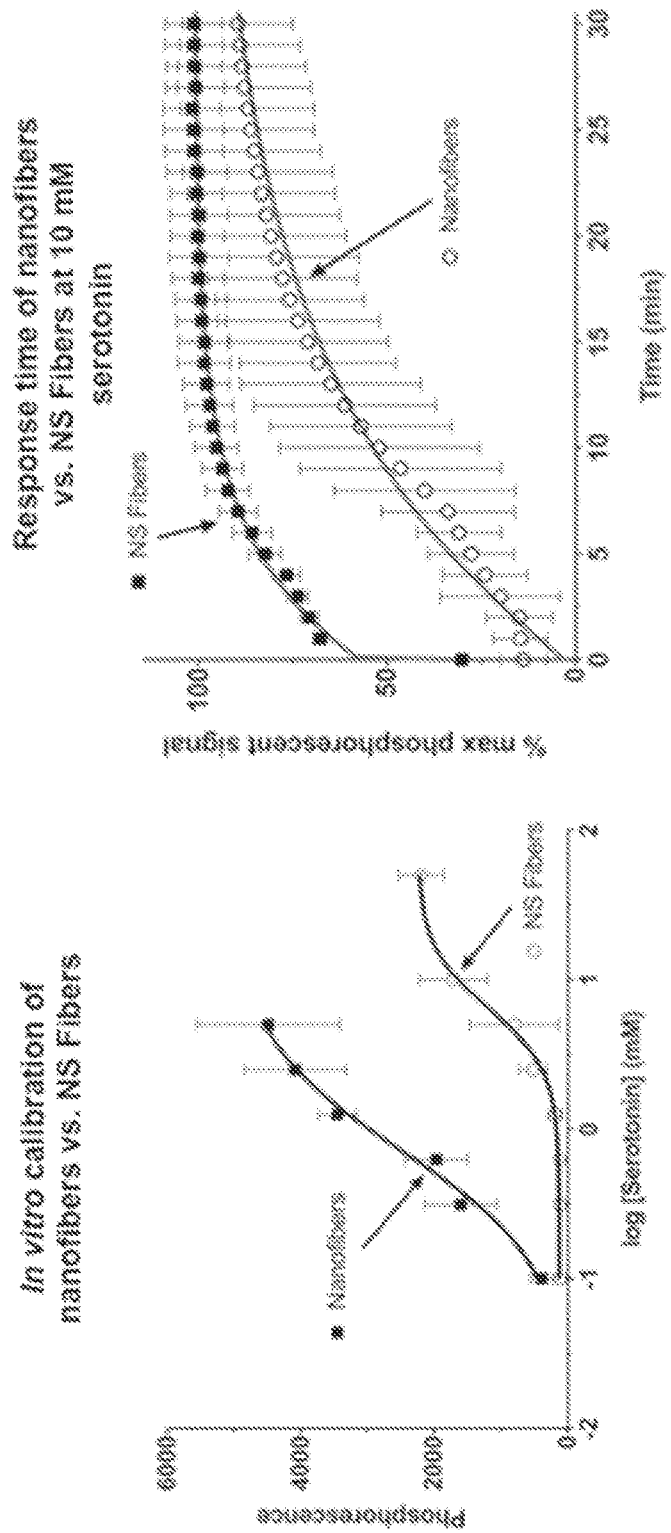
FIG. 21A is a graph showing calibration curves that indicate that NS fibers exhibit lower phosphorescence and a shifted responsive range.
FIG. 21B is graph showing that NS Fibers appear to mitigate the response time issues of nanofibers, however initial formulations do not sense serotonin in the desired range.

FIG. 21 presents a comparison of PVC-DOS nanosensors electrospun into a collagen fiber matrix (NS Fibers) with coaxially electrospun fibers. Enzyme was pipetted into solution with both of the nanofibers and the response to serotonin was examined. FIG. 21A is a graph showing calibration curves that indicate that NS fibers exhibit lower phosphorescence and a shifted responsive range. FIG. 21B is graph showing that NS Fibers appear to mitigate the response time issues of nanofibers, however initial formulations do not sense serotonin in the desired range.

Incorporating the sodium optode into the optode sensor matrix prevented diffusion of the sensor away from the spot of subcutaneous injection. Furthermore, the optode sensing agent shape and coating did not prevent optode interaction with the surrounding environment. Sensor matrices present a biocompatible mechanism to immobilize polymer sensing material in vivo for continuous monitoring. This technology can be extended to immobilize any polymer with the capacity of adjusting the hydrogel coverage or cross-linking density to alter medium interaction.

The compositions and matrices provided herein unexpectedly responded in vivo very quickly. Furthermore, it was possible to insert sensor components (namely the enzymes for recognition) into the biocompatible outer coating itself. In previous sensors, the coating only acted as a barrier and all of the sensor components were limited to the core. This allowed for detection of other analytes, such as serotonin, that could not be detected in previous systems. The nanofibers also allowed for the production of a scaffold for cell growth in vitro—not something that could be done with the microworms.

We claim:

1. A sensor matrix comprising a scaffold of nanofibers and one or more sensor components, wherein the nanofibers comprise a plasticizer, and a coaxial core and shell; the one or more sensor components are fluorescent sensors or sensors for photoacoustic imaging embedded in the nanofibers to detect an analyte; the analyte is selected from the group consisting of electrolytes, hormones, steroids, small molecules, proteases, drugs, and saccharides; and the sensor matrix has a surface area to volume ratio of at least 100 mm⁻¹ with a width of about 200 nm to about 500 nm and a length of about 1 μm to about 500 μm.

2. The sensor matrix of claim 1, wherein the one or more sensors covalently bind to the analyte, coordinate with the analyte or chelate the analyte.

3. The sensor matrix of claim 1, wherein the nanofiber comprises a polymer.

4. The sensor matrix of claim 3, wherein the polymer comprises a biocompatible polymer.

5. The sensor matrix of claim 1, wherein the shell is permeable to analyte and impermeable to the one or more sensors.

6. The sensor matrix of claim 3, wherein the nanofiber comprises one or more polymers selected from the group consisting of polycaprolactone (PCL); polylactic acid (PLA); polyethylene-co-vinyl acetate (PEVA); polyethylene oxide (PEO); polyvinylcarbazole; polyacrylic acid-polypyrene methanol (PAA-PM); cellulose acetate (CA); chitosan; fibrinogen; polyurethane; poly(lactic-co-glycolic acid) (PLGA); collagen; poly(ethylene-co-vinyl alcohol); copolymers thereof and blends thereof.

7. The sensor matrix of claim 6, wherein the nanofiber comprises one or more polymers selected from the group consisting of polycaprolactone (PCL); poly(lactic-co-glycolic acid) (PLGA); and collagen.

8. The sensor matrix of claim 1, wherein the nanofibers are present as nanowhiskers, wherein the nanowhiskers have an average length of about 1 μm to about 500 μm.

9. The sensor matrix of claim 1, wherein the sensor matrix has a length of about 40 μm to about 60 μm.

10. The sensor matrix of claim 1, wherein the nanoparticle sensor comprises an enzyme embedded in the shell.

11. The sensor matrix of claim 3, wherein the shell comprises collagen.

12. The sensor matrix of claim 1, wherein the sensor is soluble in an organic solvent.

13. The sensor matrix of claim 1, wherein the nanofiber comprises PCL or PLGA.

14. The sensor matrix of claim 1, wherein the sensor comprises a boronic acid receptor molecule.

15. A method of detecting an analyte in a tissue of a subject, the method comprising:
a) implanting a plurality of sensor matrices in the tissue, each sensor matrix comprising a scaffold of nanofibers and one or more fluorescent sensor components, wherein the nanofibers comprise a plasticizer, and a coaxial core and shell; the one or more sensor components are fluorescent sensors embedded in the nanofibers to detect an analyte; the analyte is selected from the group consisting of electrolytes, hormones, steroids, small molecules, proteases, drugs, and saccharides; wherein the device is oblong with a surface area to volume ratio of at least 100 mm⁻¹ with a width of about 200 nm to about 500 nm and a length of about 1 μm to about 500 μm:
b) contacting the plurality of sensor matrices with the analyte; and
c) detecting the analyte in the tissue of the subject.

16. The method of claim 15, wherein detecting the analyte comprises (i) exciting the one or more fluorescent sensors in the plurality of sensor matrices with an excitation energy emission from an energy emission device and (ii) detecting fluorescent energy emitted by the one or more fluorescent sensors in the plurality of sensor matrices.

17. The method of claim 16, wherein the energy emission device is a handheld device.

18. The method of claim 15, wherein implanting a plurality of sensor matrices comprises injecting the plurality of sensor matrices into the tissue.

19. The method of claim 18, wherein the tissue is selected from the group consisting of epidermal, muscular, ocular, endothelial, mucosal, dermal, subcutaneous, and organ tissues.

20. A method of detecting an analyte, the method comprising:
a) providing a plurality of sensor matrices, each sensor matrix comprising a scaffold of nanofibers and one or more sensor components, wherein the nanofiber comprises a plasticizer, and a coaxial core and shell, the one or more sensor components are fluorescent sensors or sensors for photoacoustic imaging embedded in the nanofiber to detect an analyte; the analyte is selected from the group consisting of electrolytes, hormones, steroids, small molecules, proteases, drugs, and saccharides; and at least one of the sensor components is in the shell;
b) contacting the plurality of sensor matrices with the analyte; and
c) detecting the analyte in the tissue of the subject.

* * * * *